United States Patent
Guggenheimer et al.

(10) Patent No.: US 10,213,224 B2
(45) Date of Patent: Feb. 26, 2019

(54) CLEANING DEVICE FOR CATHETER AND CATHETER INCLUDING THE SAME

(71) Applicant: Covidien LP, Mansfield, MA (US)

(72) Inventors: Ethan Guggenheimer, Minnetonka, MN (US); Zachary Garvey, Stillwater, MN (US); Lucas Schneider, Champlin, MN (US)

(*) Notice: Subject to any disclaimer, the term of this patent is extended or adjusted under 35 U.S.C. 154(b) by 489 days.

(21) Appl. No.: 14/751,288

(22) Filed: Jun. 26, 2015

(65) Prior Publication Data

US 2015/0374401 A1 Dec. 31, 2015

Related U.S. Application Data

(60) Provisional application No. 62/018,049, filed on Jun. 27, 2014.

(51) Int. Cl.
*A61B 90/70* (2016.01)
*A61B 17/3205* (2006.01)
(Continued)

(52) U.S. Cl.
CPC ........ *A61B 17/3205* (2013.01); *A61B 17/221* (2013.01); *A61B 17/320783* (2013.01);
(Continued)

(58) Field of Classification Search
CPC ........... A61M 2025/0019; B08B 9/023; A61B 90/70; A61B 2090/701
See application file for complete search history.

(56) References Cited

U.S. PATENT DOCUMENTS 1,481,078 A 1/1924 Albertson
2,178,790 A 11/1939 Henry
(Continued)

FOREIGN PATENT DOCUMENTS

CA 2000621 4/1990
DE 3732236 C1 12/1988
(Continued)

OTHER PUBLICATIONS

Brezinski et al., "Optical Coherence Tomography for Optical Biopsy," Circulation, 93:1206-1213 (1996).
(Continued)

*Primary Examiner* — Joseph L. Perrin
*Assistant Examiner* — Irina Graf
(74) *Attorney, Agent, or Firm* — Stinson Leonard Street LLP

(57) ABSTRACT

A cleaning device for cleaning a catheter lumen of a tissue removal catheter has a flushing chamber with distal and proximal seals and an inlet port. The proximal seal is a duckbill seal that includes a pair of opposing duckbill members that slidingly accept the distal end portion of a catheter body to form a seal about the catheter body proximal to a proximal opening in of the catheter lumen. Fluid is directed in the inlet port, into the flushing chamber, into proximal opening in the catheter body, and through the catheter lumen to discharge tissue contained in the catheter lumen. In some embodiments, the cleaning device is preloaded on the catheter body. The cleaning device can have an internal stop that engages with an external stop on the catheter body when the cleaning device is positioned in an operative position.

15 Claims, 15 Drawing Sheets

(51) Int. Cl.
*A61B 17/221* (2006.01)
*A61M 25/00* (2006.01)
*A61B 17/3207* (2006.01)

(52) U.S. Cl.
CPC ............ *A61B 90/70* (2016.02); *A61M 25/00* (2013.01); *A61B 2017/320791* (2013.01); *A61B 2090/701* (2016.02); *A61M 2025/0019* (2013.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,991,762 A * | 11/1976 | Radford ............ A61M 16/0463 128/200.26 |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,691,702 A * | 9/1987 | Chantzis ........... A61M 16/0463 128/207.16 |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,622 A | 3/1988 | Larsen et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,889,061 A | 12/1989 | McPherson et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kippemian |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |

(56) References Cited

U.S. PATENT DOCUMENTS

| | | | |
|---|---|---|---|
| 5,110,822 A | 5/1992 | Sherba et al. | |
| 5,112,345 A | 5/1992 | Farr | |
| 5,114,399 A | 5/1992 | Kovalcheck | |
| 5,115,814 A | 5/1992 | Griffith et al. | |
| 5,120,323 A | 6/1992 | Shockey et al. | |
| 5,127,902 A | 7/1992 | Fischell | |
| 5,127,917 A | 7/1992 | Niederhauser et al. | |
| 5,135,531 A | 8/1992 | Shiber | |
| 5,154,705 A | 10/1992 | Fleischhacker et al. | |
| 5,154,724 A | 10/1992 | Andrews | |
| 5,165,421 A | 11/1992 | Fleischhacker et al. | |
| 5,176,693 A | 1/1993 | Pannek, Jr. | |
| 5,178,625 A | 1/1993 | Groshong | |
| 5,181,920 A | 1/1993 | Mueller et al. | |
| 5,183,432 A | 2/1993 | Noguchi | |
| 5,190,528 A | 3/1993 | Fonger et al. | |
| 5,192,291 A | 3/1993 | Pannek, Jr. | |
| 5,195,956 A | 3/1993 | Stockmeier | |
| 5,211,651 A | 5/1993 | Reger et al. | |
| 5,217,474 A | 6/1993 | Zacca et al. | |
| 5,222,966 A | 6/1993 | Perkins et al. | |
| 5,224,488 A | 7/1993 | Neuffer | |
| 5,224,945 A | 7/1993 | Pannek, Jr. | |
| 5,224,949 A | 7/1993 | Gomringer et al. | |
| 5,226,909 A | 7/1993 | Evans et al. | |
| 5,226,910 A | 7/1993 | Kajiyama et al. | |
| 5,234,451 A | 8/1993 | Osypka | |
| 5,242,428 A * | 9/1993 | Palestrant | A61M 25/01 |
| | | | 604/265 |
| 5,242,460 A | 9/1993 | Klein et al. | |
| 5,242,461 A | 9/1993 | Kortenbach et al. | |
| 5,250,059 A | 10/1993 | Andreas et al. | |
| 5,250,065 A | 10/1993 | Clement et al. | |
| 5,263,928 A | 11/1993 | Trauthen et al. | |
| 5,263,959 A | 11/1993 | Fischell | |
| 5,267,955 A | 12/1993 | Hanson | |
| 5,267,982 A | 12/1993 | Sylvanowicz | |
| 5,269,793 A | 12/1993 | Simpson et al. | |
| 5,273,526 A | 12/1993 | Dance et al. | |
| 5,282,484 A | 2/1994 | Reger | |
| 5,284,486 A | 2/1994 | Kotula et al. | |
| 5,285,795 A | 2/1994 | Ryan et al. | |
| 5,295,493 A | 3/1994 | Radisch, Jr. | |
| 5,300,085 A | 4/1994 | Yock | |
| 5,306,294 A | 4/1994 | Winston et al. | |
| 5,308,354 A | 5/1994 | Zacca et al. | |
| 5,312,425 A | 5/1994 | Evans et al. | |
| 5,312,427 A | 5/1994 | Shturman | |
| 5,314,438 A | 5/1994 | Shturman | |
| 5,318,032 A | 6/1994 | Lonsbury et al. | |
| 5,318,528 A | 6/1994 | Heaven et al. | |
| 5,318,576 A | 6/1994 | Plassche, Jr. et al. | |
| 5,321,501 A | 6/1994 | Swanson et al. | |
| 5,322,508 A | 6/1994 | Viera | |
| 5,333,606 A * | 8/1994 | Schneider | A61M 1/0064 |
| | | | 128/200.24 |
| 5,350,390 A | 9/1994 | Sher | |
| 5,356,418 A | 10/1994 | Shturman | |
| 5,358,472 A | 10/1994 | Vance et al. | |
| 5,358,485 A | 10/1994 | Vance et al. | |
| 5,360,432 A | 11/1994 | Shturman | |
| 5,366,463 A | 11/1994 | Ryan | |
| 5,368,035 A | 11/1994 | Hamm et al. | |
| 5,370,609 A | 12/1994 | Drasler et al. | |
| 5,370,651 A | 12/1994 | Summers | |
| 5,372,601 A | 12/1994 | Lary | |
| 5,372,602 A | 12/1994 | Burke | |
| 5,373,619 A | 12/1994 | Fleischhacker et al. | |
| 5,373,849 A | 12/1994 | Maroney et al. | |
| 5,377,682 A | 1/1995 | Ueno et al. | |
| 5,378,234 A | 1/1995 | Hammerslag et al. | |
| 5,383,460 A | 1/1995 | Jang et al. | |
| 5,395,311 A | 3/1995 | Andrews | |
| 5,395,313 A | 3/1995 | Naves et al. | |
| 5,395,335 A | 3/1995 | Jang | |
| 5,397,345 A | 3/1995 | Lazarus | |
| 5,402,790 A | 4/1995 | Jang et al. | |
| 5,403,334 A | 4/1995 | Evans et al. | |
| 5,409,454 A | 4/1995 | Fischell et al. | |
| 5,413,107 A | 5/1995 | Oakley et al. | |
| 5,419,774 A | 5/1995 | Willard et al. | |
| 5,423,740 A | 6/1995 | Sullivan | |
| 5,423,799 A | 6/1995 | Shiu | |
| 5,423,838 A | 6/1995 | Willard | |
| 5,423,846 A | 6/1995 | Fischell | |
| 5,427,107 A | 6/1995 | Milo et al. | |
| 5,429,136 A | 7/1995 | Milo et al. | |
| 5,431,673 A | 7/1995 | Summers et al. | |
| 5,441,510 A | 8/1995 | Simpson et al. | |
| 5,443,446 A | 8/1995 | Shturman | |
| 5,443,497 A | 8/1995 | Venbrux | |
| 5,444,078 A | 8/1995 | Yu et al. | |
| 5,445,155 A | 8/1995 | Sieben | |
| 5,449,369 A | 9/1995 | Imran | |
| 5,451,233 A | 9/1995 | Yock | |
| 5,454,809 A | 10/1995 | Janssen | |
| 5,456,667 A | 10/1995 | Ham et al. | |
| 5,456,689 A | 10/1995 | Kresch et al. | |
| 5,458,585 A | 10/1995 | Salmon et al. | |
| 5,459,570 A | 10/1995 | Swanson et al. | |
| 5,464,016 A | 11/1995 | Nicholas et al. | |
| 5,470,415 A | 11/1995 | Perkins et al. | |
| 5,485,042 A | 1/1996 | Burke et al. | |
| 5,485,840 A | 1/1996 | Bauman | |
| 5,487,729 A | 1/1996 | Avellanet et al. | |
| 5,489,295 A | 2/1996 | Piplani et al. | |
| 5,491,524 A | 2/1996 | Hellmuth et al. | |
| 5,496,267 A | 3/1996 | Drasler et al. | |
| 5,501,694 A | 3/1996 | Ressemann et al. | |
| 5,503,155 A | 4/1996 | Salmon et al. | |
| 5,505,210 A | 4/1996 | Clement | |
| 5,507,292 A | 4/1996 | Jang et al. | |
| 5,507,760 A | 4/1996 | Wynne et al. | |
| 5,507,761 A | 4/1996 | Duer | |
| 5,507,795 A | 4/1996 | Chiang et al. | |
| 5,512,044 A | 4/1996 | Duer | |
| 5,514,115 A | 5/1996 | Frantzen et al. | |
| 5,520,189 A | 5/1996 | Malinowski et al. | |
| 5,522,825 A | 6/1996 | Kropf et al. | |
| 5,522,880 A | 6/1996 | Barone et al. | |
| 5,527,292 A | 6/1996 | Adams et al. | |
| 5,527,298 A | 6/1996 | Vance et al. | |
| 5,527,325 A | 6/1996 | Conley et al. | |
| 5,531,685 A | 7/1996 | Hemmer et al. | |
| 5,531,690 A | 7/1996 | Solar | |
| 5,531,700 A | 7/1996 | Moore et al. | |
| 5,540,707 A | 7/1996 | Ressemann et al. | |
| 5,549,601 A | 8/1996 | McIntyre et al. | |
| 5,554,163 A | 9/1996 | Shturman | |
| 5,556,408 A | 9/1996 | Farhat | |
| 5,558,093 A | 9/1996 | Pomeranz | |
| 5,562,726 A | 10/1996 | Chuter | |
| 5,562,728 A | 10/1996 | Lazarus et al. | |
| 5,569,275 A | 10/1996 | Kotula et al. | |
| 5,569,276 A | 10/1996 | Jang et al. | |
| 5,569,277 A | 10/1996 | Evans et al. | |
| 5,569,279 A | 10/1996 | Rainin | |
| 5,570,693 A | 11/1996 | Jang et al. | |
| 5,571,122 A | 11/1996 | Kelly et al. | |
| 5,571,130 A | 11/1996 | Simpson et al. | |
| 5,575,817 A | 11/1996 | Martin | |
| 5,584,842 A | 12/1996 | Fogarty et al. | |
| 5,584,843 A | 12/1996 | Wulfman et al. | |
| 5,609,605 A | 3/1997 | Marshall et al. | |
| 5,618,293 A | 4/1997 | Sample et al. | |
| 5,620,447 A | 4/1997 | Smith et al. | |
| 5,624,457 A | 4/1997 | Farley et al. | |
| 5,626,562 A | 5/1997 | Castro | |
| 5,626,576 A | 5/1997 | Janssen | |
| 5,628,761 A | 5/1997 | Rizik | |
| 5,632,754 A | 5/1997 | Farley et al. | |
| 5,632,755 A | 5/1997 | Nordgren et al. | |
| 5,634,464 A | 6/1997 | Jang et al. | |
| 5,643,296 A | 7/1997 | Hundertmark et al. | |

(56) References Cited

U.S. PATENT DOCUMENTS

| | | |
|---|---|---|
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,755,894 A | 5/1998 | Bowman et al. |
| 5,766,192 A | 6/1998 | Zacca |
| 5,772,674 A | 6/1998 | Nakhjavan |
| 5,775,325 A * | 7/1998 | Russo ............... A61M 16/0463 128/202.27 |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,979,951 A | 11/1999 | Shimura |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,016,649 A | 1/2000 | Bock et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |

(56) References Cited

U.S. PATENT DOCUMENTS

| | | |
|---|---|---|
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfrnan et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,226,675 B2 | 7/2012 | Simpson et al. |
| 9,532,844 B2 * | 1/2017 | Garvey ............... A61B 90/70 |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | Van Tassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0065450 A1* | 5/2002 | Ogawa ............... A61B 1/00087 600/157 |
| 2002/0077373 A1 | 6/2002 | Hudson |
| 2002/0077642 A1 | 6/2002 | Patel et al. |
| 2002/0095141 A1 | 6/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michltsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0020165 A1* | 1/2006 | Adams ............... A61B 1/00094 600/121 |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0215190 A1 | 9/2007 | Efinger et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |

(56) References Cited

U.S. PATENT DOCUMENTS

| | | | |
|---|---|---|---|
| 2008/0004646 A1 | 1/2008 | To et al. | |
| 2008/0004647 A1 | 1/2008 | To et al. | |
| 2008/0045986 A1 | 2/2008 | To et al. | |
| 2008/0051735 A1* | 2/2008 | Measamer | A61B 1/00087 604/265 |
| 2008/0051812 A1 | 2/2008 | Schmitz et al. | |
| 2008/0065124 A1 | 3/2008 | Olson | |
| 2008/0065125 A1 | 3/2008 | Olson | |
| 2008/0097403 A1 | 4/2008 | Donaldson et al. | |
| 2008/0125799 A1 | 5/2008 | Adams | |
| 2008/0161840 A1 | 7/2008 | Osiroff et al. | |
| 2008/0177139 A1 | 7/2008 | Courtney et al. | |
| 2008/0208227 A1 | 8/2008 | Kadykowski et al. | |
| 2008/0249553 A1 | 10/2008 | Gruber et al. | |
| 2008/0312673 A1 | 12/2008 | Viswanathan et al. | |
| 2009/0012548 A1 | 1/2009 | Thatcher et al. | |
| 2009/0018565 A1 | 1/2009 | To et al. | |
| 2009/0018566 A1 | 1/2009 | Escudero et al. | |
| 2009/0138031 A1 | 5/2009 | Tsukernik et al. | |
| 2009/0187203 A1 | 7/2009 | Corvi et al. | |
| 2009/0216125 A1 | 8/2009 | Lenker | |
| 2009/0216180 A1 | 8/2009 | Lee et al. | |
| 2009/0226063 A1 | 9/2009 | Rangwala et al. | |
| 2009/0234378 A1 | 9/2009 | Escudero et al. | |
| 2009/0270818 A1* | 10/2009 | Duke | A61B 17/3421 604/272 |
| 2009/0270888 A1 | 10/2009 | Patel et al. | |
| 2009/0275966 A1 | 11/2009 | Mitusina | |
| 2009/0299394 A1 | 12/2009 | Simpson et al. | |
| 2009/0306689 A1 | 12/2009 | Welty et al. | |
| 2010/0030216 A1 | 2/2010 | Arcenio | |
| 2010/0049225 A1 | 2/2010 | To et al. | |
| 2010/0130996 A1 | 5/2010 | Doud et al. | |
| 2010/0198240 A1 | 8/2010 | Simpson et al. | |
| 2010/0241147 A1 | 9/2010 | Maschke | |
| 2010/0280534 A1 | 11/2010 | Sher | |
| 2010/0292721 A1 | 11/2010 | Moberg | |
| 2010/0298850 A1 | 11/2010 | Snow et al. | |
| 2010/0312263 A1 | 12/2010 | Moberg et al. | |
| 2010/0331787 A1* | 12/2010 | Fournie | A61M 39/1011 604/207 |
| 2011/0004107 A1 | 1/2011 | Rosenthal et al. | |
| 2011/0022069 A1 | 1/2011 | Mitusina | |
| 2011/0040315 A1 | 2/2011 | To et al. | |
| 2011/0046449 A1* | 2/2011 | Minnelli | A61B 1/00128 600/205 |
| 2011/0130777 A1 | 6/2011 | Zhang et al. | |
| 2011/0144673 A1 | 6/2011 | Zhang et al. | |
| 2011/0275974 A1* | 11/2011 | Valaie | A61M 25/00 604/6.16 |
| 2012/0238816 A1* | 9/2012 | Gunday | A61B 1/00135 600/114 |
| 2012/0330336 A1 | 12/2012 | Simpson et al. | |
| 2013/0081660 A1* | 4/2013 | Roberts | A61L 2/18 134/94.1 |
| 2013/0150674 A1* | 6/2013 | Haig | A61B 1/00131 600/155 |
| 2014/0166054 A1 | 6/2014 | Moberg | |
| 2014/0316380 A1* | 10/2014 | Davis | A61M 1/3653 604/508 |
| 2015/0190041 A1* | 7/2015 | Suehara | A61B 1/00135 600/109 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 9316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |

OTHER PUBLICATIONS

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

International Search Report and Written Opinion for Application

(56) References Cited

OTHER PUBLICATIONS

No. PCT/US2015/037800, dated Sep. 10, 2015, 10 pages, Rijswijk, NL.

* cited by examiner

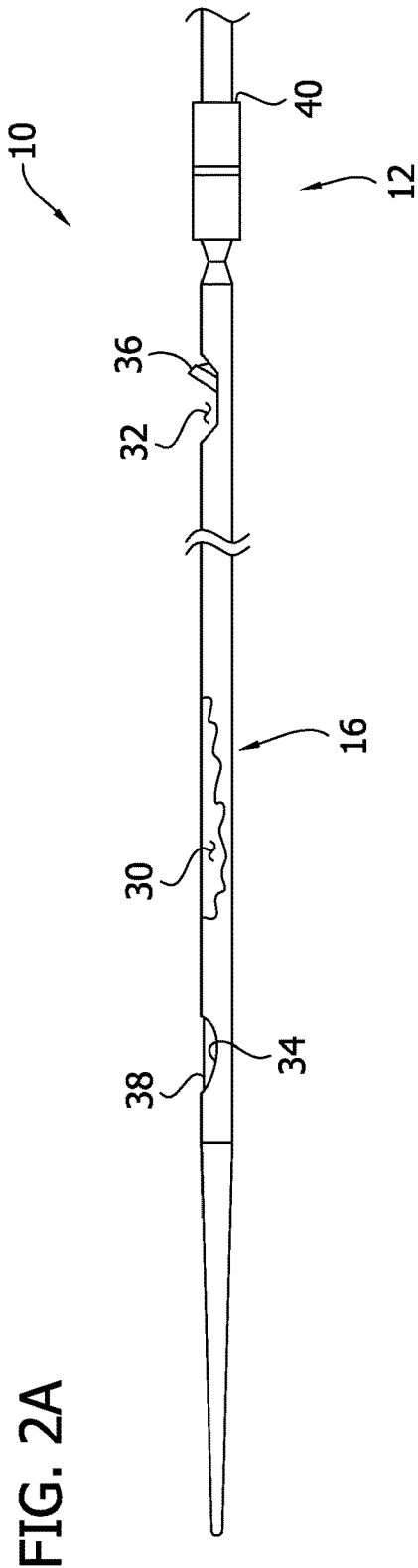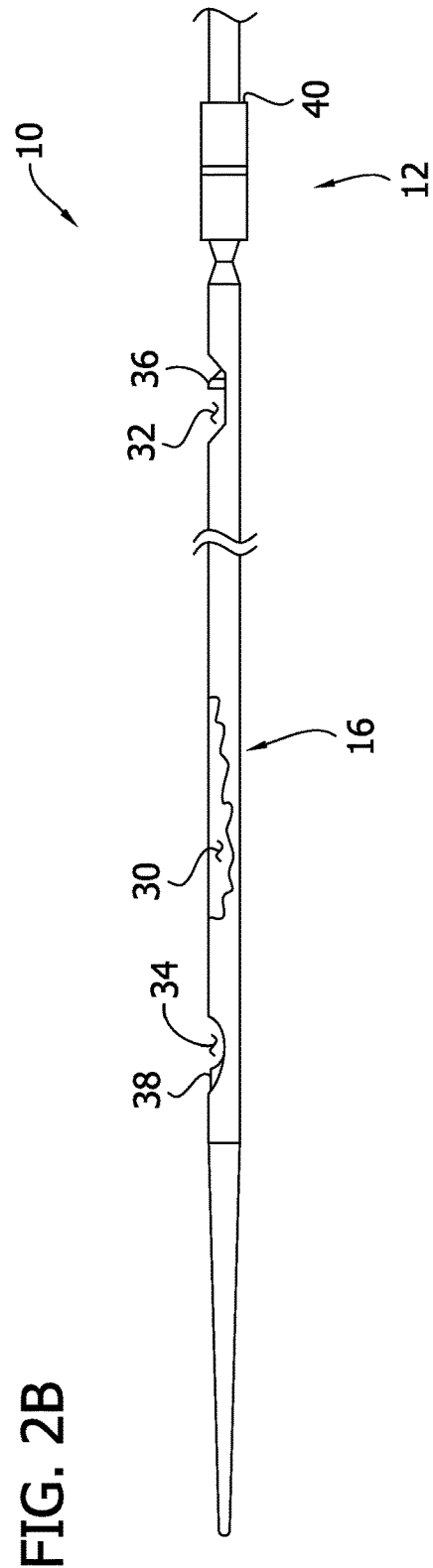

US 10,213,224 B2

CLEANING DEVICE FOR CATHETER AND CATHETER INCLUDING THE SAME

CROSS REFERENCE TO RELATED APPLICATIONS

This application claims priority to U.S. Provisional Patent Application Ser. No. 62/018,049, filed Jun. 27, 2014, the entirety of which is hereby incorporated by reference.

FIELD OF THE DISCLOSURE

Aspects of the present disclosure generally relate to a cleaning device for cleaning a catheter.

BACKGROUND OF THE DISCLOSURE

Certain medical devices such as tissue removal catheters require cleaning to remove collected debris. For example, some tissue removal catheters include a tissue collection chamber that collects excised tissue and other debris that is cut away or otherwise extracted from a vascular or other biological lumen. When tissue collection chambers become full they can be cleaned to empty the collected tissue. Certain cleaning tools have been developed to aid in cleaning the tissue collection chambers of tissue removal catheters. In one example, a cleaning tool is received on the distal tip of an atherectomy catheter until it visually appears that the device is in an operative position. A proximal Touhy Borst seal of the cleaning tool is manually actuated to seal a flushing lumen of the cleaning device about the catheter, and flushing fluid is imparted into the flushing lumen.

SUMMARY OF THE DISCLOSURE

In one aspect a cleaning device for cleaning tissue from a catheter lumen of a tissue removal catheter includes a proximal duckbill seal that forms a passive fluid seal with the catheter body of the catheter.

In another aspect a catheter includes a preloaded cleaning device. The cleaning device is slidable from a preloaded position at a proximal end portion of the catheter body to an operative position at a distal end portion of the catheter body.

In another aspect a cleaning device for cleaning tissue from a catheter lumen of a tissue removal catheter includes a one-piece flushing chamber with interlocking features for securing at least one duckbill seal to the flushing chamber.

In another aspect a seal for sealing a cleaning device for cleaning tissue from a catheter lumen of a tissue removal catheter around the catheter includes a sealing skirt configured to sealingly engage a flushing chamber of the cleaning device and be exposed to flushing fluid that, when pressurized, enhances the sealing engagement between the sealing skirt and flushing chamber.

In another aspect a cleaning device for cleaning tissue from a catheter lumen of a tissue removal catheter includes a flushing chamber with bendable tabs that bend inward to form a retention lip adjacent one end of flushing chamber for securing a seal to the flushing chamber.

Other features will be in part apparent and in part pointed out hereinafter.

BRIEF DESCRIPTION OF THE DRAWINGS

FIG. 2A is an enlarged view of a distal end portion of the catheter having a portion thereof broken away to reveal a catheter lumen;

FIG. 2B is similar to FIG. 2A illustrating the distal end portion of the catheter in a different configuration;

Corresponding reference characters indicate corresponding parts throughout the drawings.

DETAILED DESCRIPTION

Figure 1:
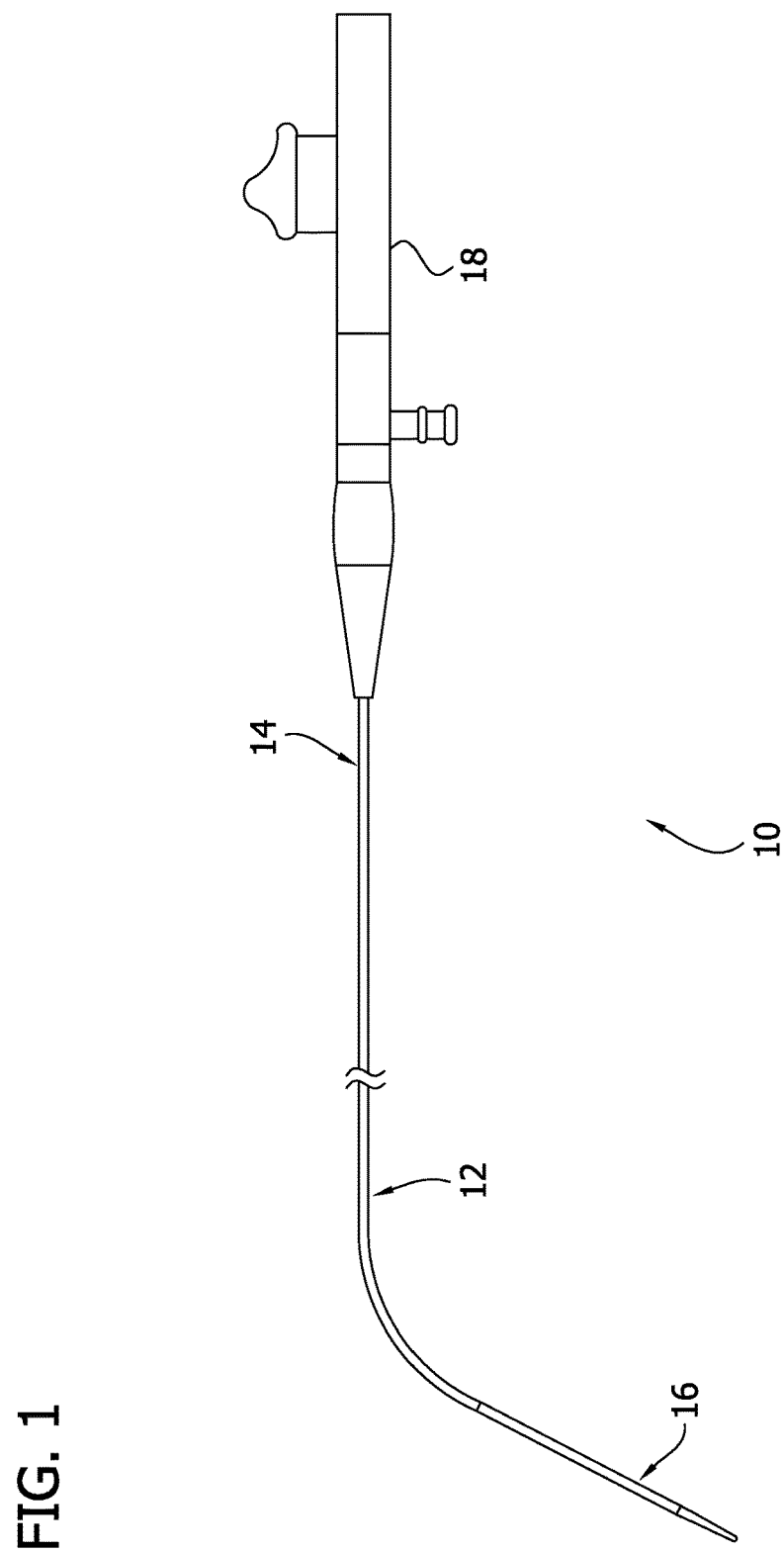
FIG. 1 is a schematic of a catheter suitable for cleaning with a cleaning device.

Referring to FIG. 1, a catheter is generally indicated at reference number 10. The catheter 10 includes an elongate catheter body 12 that is sized to be inserted in a biological lumen to extract and remove tissue and other luminal debris. Examples of biological lumens include but are not limited to an artery, vein, thrombus, etc. The catheter body 12 has a proximal end portion generally indicated at 14 and a distal end portion generally indicated at 16. A handle adaptor 18 is attached to the proximal end portion 14. In the illustrated embodiment the handle adaptor is configured to receive a handle (not shown) thereupon. In the illustrated embodiment, the handle and handle adaptor 18 include various features that can be used to control the catheter 10 in use. The illustrated catheter 10 is an atherectomy catheter, though it is contemplated that other types of catheters can also be used without departing from the scope of the invention. In general, the catheter body 12 is configured to be inserted in a biological lumen to remove tissue. In the illustrated embodiment, the distal end portion 14 of the catheter body 12 is configured to be inserted into an arterial lumen first. The distal end portion 16 of the catheter body 12 is configured to extract and remove tissue as described in further detail below.

As shown in FIG. 2A, the distal end portion 16 of the catheter body 12 defines a catheter lumen 30 that extends from a proximal opening 32 to a distal opening 34. The catheter lumen 30 is in fluid communication with the proximal opening 32 and the distal opening 34. In the illustrated embodiment, the proximal opening 32 is a cutter window. A cutting element 36 is configured to extend through the cutter window 32 and engage tissue on the wall of the biological lumen. The cutting element 36 is configured to rotate at a relatively high speed to slice through tissue in the biological lumen. The catheter body 12 is configured to slide through the biological lumen in the distal direction as the cutting element 36 rotates. The catheter 10 is configured such that rotational motion of the cutting element 36 and the translational motion of the catheter body 12 direct cut tissue in the distal direction toward the catheter lumen 30. Thus, in the illustrated embodiment, the catheter lumen 30 is a tissue collection chamber. In FIG. 2A, the distal opening 34 is illustrated covered by a scoop 38. In this configuration the scoop 38 is positioned to prevent cut tissue from escaping from the tissue collection chamber 30 out the distal opening 34. When the tissue collection chamber 30 is full, the catheter body 12 is configured to be drawn out of the arterial lumen so the cut tissue can be flushed from the tissue collection chamber and discarded. As shown in FIG. 2B, the scoop 38 is configured to be rotated to open the distal opening 34 so that the tissue contained in the tissue collection chamber 30 can be flushed out through the distal opening. In addition, the cutting element 36 is movable relative to the catheter body 12 so it can be drawn into the cutter window 32, as shown in FIG. 2B.

The distal end portion 16 of the catheter body 12 also includes an external stop 40. The external stop 40 is disposed proximal to the proximal opening 32. In the illustrated embodiment, the external stop 40 is part of a torque shaft adapter that links a torque shaft of the catheter 10 to the distal end portion 16. However, in other embodiments the external stop can be other components (e.g., a single-purpose stop) without departing from the scope of the invention. As will be discussed in greater detail below, the external stop 40 is configured to engage with a corresponding feature of a cleaning device to align the cleaning device in an operative position in which the cleaning device can flush cut tissue from the tissue collection chamber 30.

Figure 3:
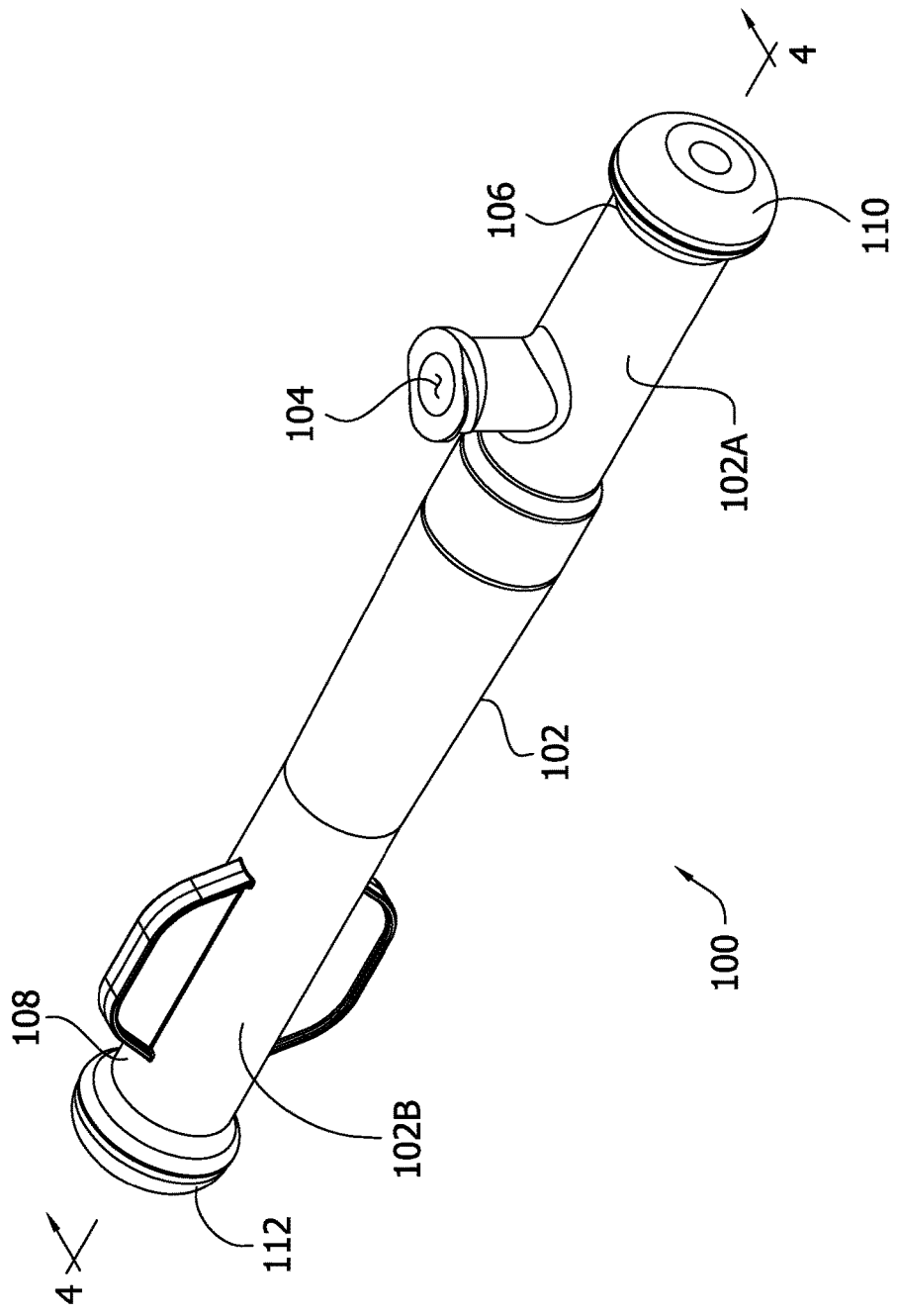
FIG. 3 is a perspective view of a cleaning device.

Referring to FIG. 3, an embodiment of a cleaning device for cleaning the tissue collection chamber 30 is indicated generally at reference number 100. The cleaning device 100 has a generally cylindrical flushing chamber 102 comprising a proximal chamber member 102A and a distal chamber member 102B attached to the proximal chamber member, such as by adhesive, welding, or mechanical fastening. A fluid inlet port 104 extends outwardly from a central portion of the flushing chamber 102. The fluid inlet port 104 is configured to fluidly connect to a source of flushing fluid (not shown). For example, in some embodiments, the fluid inlet port 104 can be a luer tip configured to receive a corresponding luer tip of a source of flushing fluid, such as a syringe. It will be understood, that other fluid inlet port configurations can also be used without departing from the scope of the invention. The flushing chamber 102 has an open proximal end 106 and an open distal end 108. A proximal seal 110 is connected to the open proximal end 106 of the flushing chamber 102, and a distal seal 112 is connected to the open distal end 108 of the flushing chamber.

Figure 4:
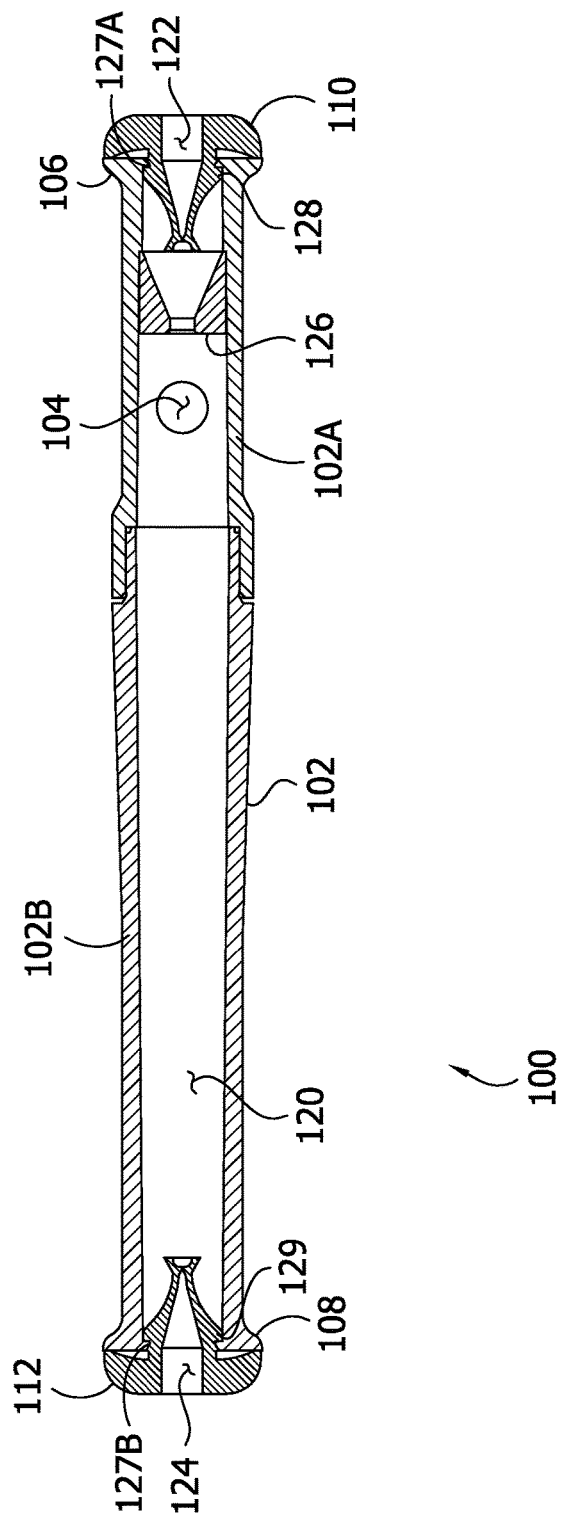
FIG. 4 is a section view taken in the plane 4-4 of FIG. 3.

As shown in FIG. 4, the flushing chamber 102 of the cleaning device 100 defines a flushing lumen 120. The flushing lumen 120 extends between the proximal and distal ends 106, 108 of the flushing chamber 102, and the inlet port 104 is in fluid communication with the flushing lumen. Fluid dispensed through the inlet port 104 enters the flushing lumen 120. As will be explained in further detail below, the flushing lumen 120 is configured to accept the distal end portion 16 of the catheter body 12 therein through the proximal end thereof. An internal stop 126 is secured to the cleaning device 100 inside the flushing lumen 100. In the illustrated embodiment, the internal stop 126 is a separate component from the flushing chamber 102. It is secured to the chamber 102 with an ultraviolet tack bond. However, it should be understood that the internal stop 126 can be secured within the flushing chamber 120 in other ways without departing from the scope of the invention. For example, in some embodiments the internal stop can be integrally formed with the flushing chamber. As will be discussed in greater detail below, the internal stop 126 is configured, in the illustrated embodiment, to engage with the external stop 40 of the catheter body 12 to align the cleaning device 100 in an operative position with respect to the catheter body.

Referring still to FIG. 4, the proximal and distal seals 110, 112 are each secured to a respective end 106, 108 of the chamber 102. The proximal seal 110 is a duckbill seal that is sealingly received in the flushing lumen 120 at a location proximal to the inlet port 104. In the illustrated embodiment, the proximal duckbill seal 110 is sealingly received in the open proximal end 106 of the flushing chamber 102. The proximal chamber member 102A includes an annular seal mounting flange or lip 127A that extends radially inward into the interior of the chamber adjacent the proximal end 106. The proximal seal 110 defines a radially outwardly extending flange or shoulder 128 (also shown in FIGS. 5 and 6) that engages the annular seal mounting lip 127A when the proximal seal is sealingly received in the flushing lumen and secured to the chamber 102. The engagement between the lip 127A and the shoulder 128 inhibits the seal 110 from being discharged proximally out the open proximal end 106 of the chamber when the flushing lumen 120 is pressurized with flushing fluid. The distal seal 112 of the illustrated cleaning device 100 is also a duckbill seal. The distal duckbill seal 112 is sealingly received in the flushing lumen 120 at a location distal to the inlet port 104. In the illustrated embodiment, the distal duckbill seal 112 is sealingly received in the open distal end 108 of the flushing chamber 102. The distal chamber member 102B includes an annular seal mounting flange or lip 127B that extends radially inward into the interior of the chamber adjacent the distal end 108. The distal seal 112 defines a radially outwardly extending shoulder 129 that engages the annular seal mounting lip 127B when the proximal seal is sealingly received in the flushing lumen and secured to the chamber 102. The engagement between the lip 127B and the shoulder 129 inhibits the seal 110 from being discharged proximally out the open proximal end 106 of the chamber when the flushing lumen 120 is pressurized with flushing fluid.

In one or more embodiments, the flushing chamber 102 is formed in an injection molding, casting, or other molding process. In the illustrated embodiment, each of the chamber members 102A, 102B is formed separately. A core pin is used to form the flushing lumen 120 and the seal mounting lip 127A, 127B of each respective chamber member 102A, 102B.

Each of the duckbill seals 110, 112 has a sealing passage 122, 124. In the illustrated embodiment, the duckbill seals 110, 112 are secured to the flushing chamber 102 such that the longitudinal axes of the sealing passages 122, 124 are aligned. As will be discussed in greater detail below, the duckbill seals 110, 112 are configured to receive the distal end portion 16 of the catheter body 12 in the sealing passages 122, 124 such that the distal end portion of the catheter body extends through the flushing lumen 120 in an operative position. Though the illustrated embodiment uses two duckbill seals for the proximal and distal seals 110 and 112, it should be understood that other types of seals can also be used without departing from the scope of the invention.

Figure 5:
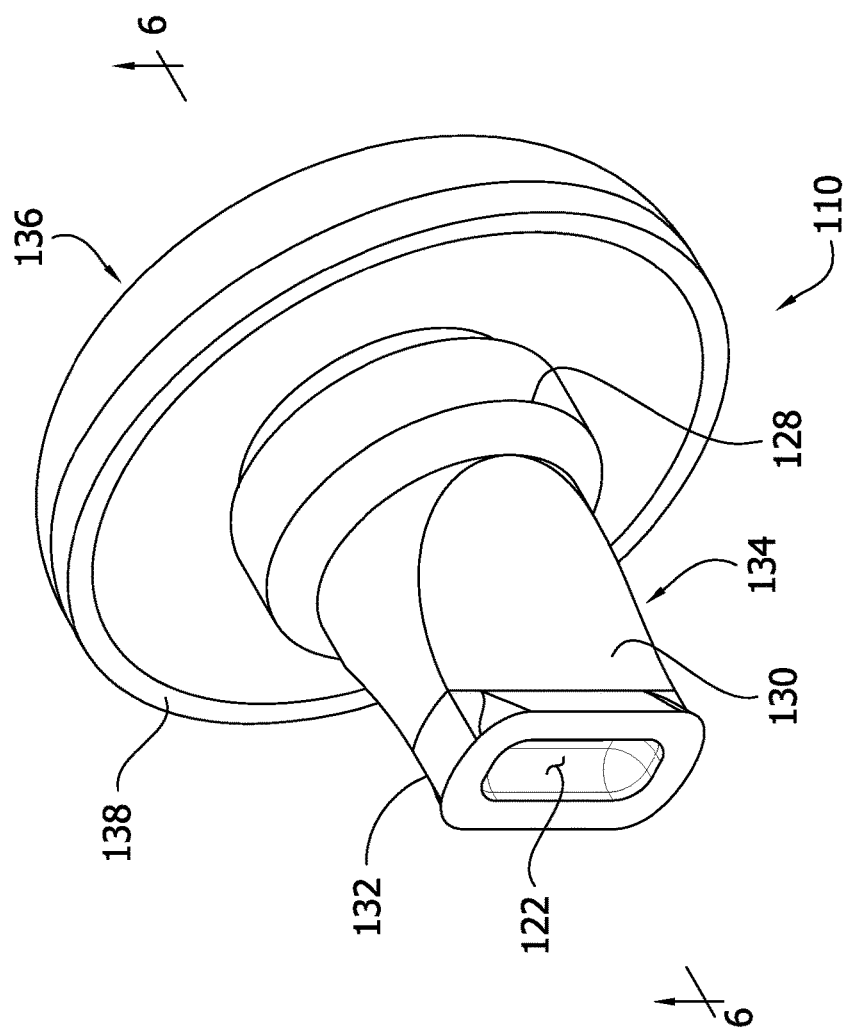
FIG. 5 is a perspective view of a duckbill seal.

Referring to FIG. 5, the proximal duckbill seal 110 includes a pair of opposing duckbill members 130, 132. The opposing duckbill members 130, 132 are configured to slidingly accept therebetween the distal end portion 16 of the catheter body 12 to form a fluid seal about the catheter body proximal to the proximal opening 32 of the catheter body. For example, in some embodiments the duckbill seal 110 forms a liquid-tight seal about the catheter body 112, and in other embodiments the duckbill seal forms a hermetic seal about the catheter body 112. In the illustrated embodiment, the sealing passage 122 passes between the opposed duckbill members 130, 132. Together, the duckbill members 130, 132 form a tapered end 134 of the duckbill seal 110. The tapered end 134 of the proximal duckbill seal 110 is configured to be received within the open proximal end 106 of the flushing chamber 102. Preferably, an outer surface of the tapered end 134 of the duckbill seal 110 compressively engages an inner surface of the fluid chamber 102 to secure the seal in place with respect to the flushing lumen 120 and seal it therein. An external end 136 of the proximal duckbill seal 110 extends radially outward from the wider end of the tapered end 134 to define a radial shoulder 138. The shoulder 138 is configured to engage an external surface of the open proximal end 106 of the flushing chamber 102. In the illustrated embodiment, the proximal duckbill seal 110 comprises a one-piece body of elastomeric material. Preferably, the duckbill seal 110 is made from a resilient material. It will be understood, however, that other materials and constructions can also be used without departing from the scope of the invention.

Figure 6:
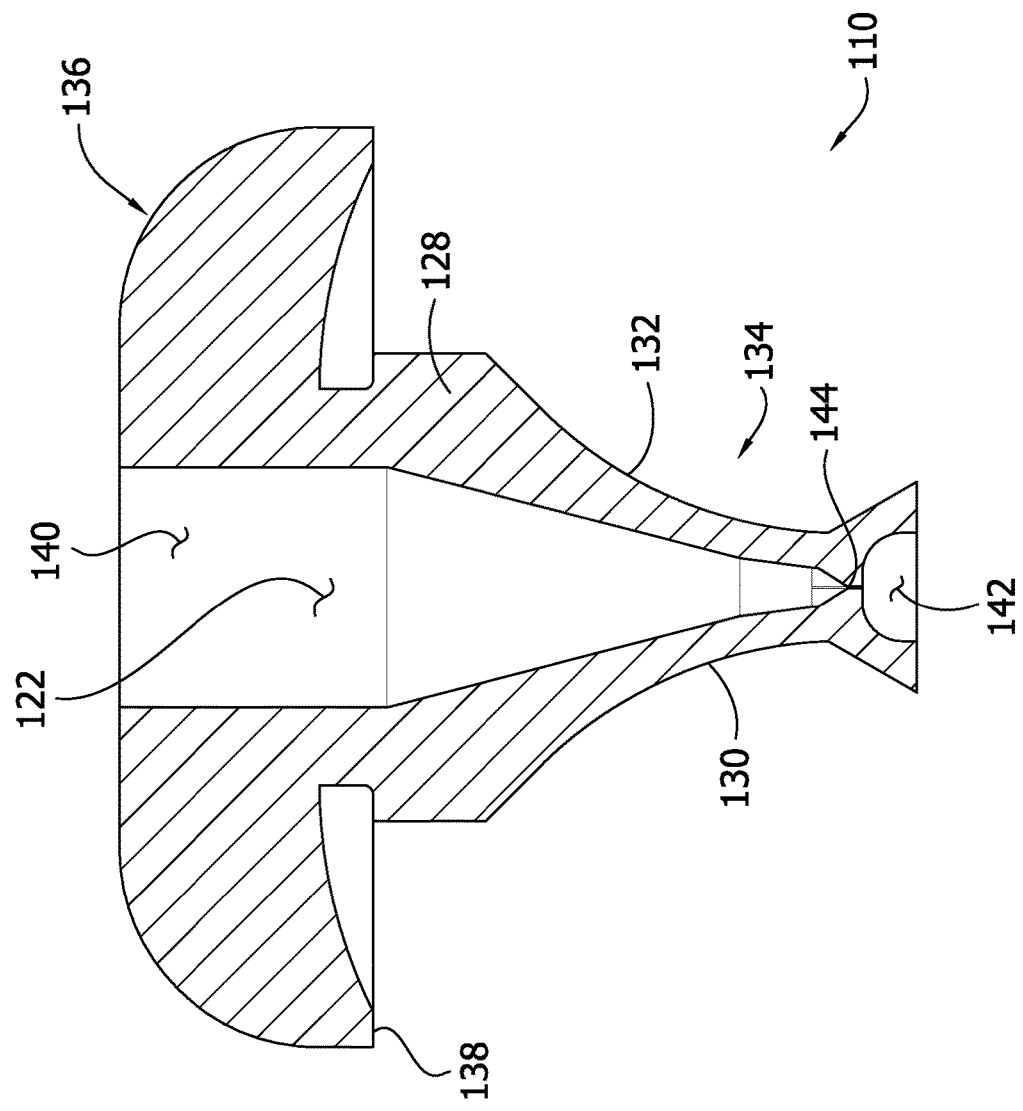
FIG. 6 is a section view taken in the plane 6-6 of FIG. 5.

As shown in FIG. 6, the sealing passage 122 of the proximal duckbill seal 110 has an open proximal end 140 disposed in the external end 136 of the seal. Likewise, the sealing passage 122 of the proximal duckbill seal 110 has an open distal end 142 disposed in the tapered end 134 of the proximal duckbill seal. The sealing passage 122 is generally tapered from its proximal end 140 to its distal end 142 such that the open proximal end 140 of the passage defines a larger opening than the open distal end 142. The proximal duckbill seal 110 is configured to form a liquid-tight seal about the catheter body 12 at a sealing band 144 at which the sealing passage 122 defines an opening having an equilibrium cross-sectional area that is smaller than a cross-sectional area of the catheter body 12 received in the proximal duckbill seal when the cleaning device 100 is in the operative position. "Equilibrium cross-sectional area" means the cross-sectional area of the opening when no force is applied to the duckbill seal 110 that affects the cross-sectional shape of the sealing passage 122. In the illustrated embodiment, the sealing band 144 defines a slit. However, it should be understood that sealing bands can also define larger openings without departing from the scope of the invention. The opening of the sealing band 144 may have a sealing cross-sectional area that compressively conforms to the cross-sectional shape of the catheter body 12 that is received in the proximal duckbill seal 110 when the cleaning device 100 is in the operative position. The resilient material of the proximal duckbill seal 110 suitably forms a fluid-tight interface with the distal end portion 16 of the catheter body 12 when the cleaning device 100 is in the operative position.

The resilient duckbill seal 110 forms a liquid-tight seal with the catheter body 12 as soon as it is placed in the operative position. It is a passive seal that requires no additional sealing actuation other than the force applied to position the cleaning device 100 in the operative position. Because the sealing band 144 of the proximal duckbill seal 110 has an opening having an equilibrium cross-sectional area that is smaller than the cross-sectional shape of the catheter body 12, the resilient material of the seal conforms to the shape of the catheter body as it slides into the operative position. The compressive force of the resilient material is alone enough to create a liquid tight seal with the catheter body 12. Thus, the user of the cleaning device 100 only has to perform one step to form a liquid-tight seal with the catheter body 12 at the proximal end 106 of the flushing chamber 102: slide the cleaning device into the operative position. The duckbill seal 110 is axially fixed with respect to the flushing chamber 102. No portion of the of the duckbill seal 110 moves axially with respect to the flushing chamber 102 in order to form a liquid-tight seal. These features reduce the time and effort required for cleaning the tissue collection chamber 30 of the catheter body 12 when performing a procedure such as atherectomy.

In the illustrated embodiment of a cleaning tool 100, the distal seal 112 is substantially identical to the proximal duckbill seal 110. Thus, the distal duckbill seal 112 is sealingly received in the flushing lumen 120 of the cleaning device 100 at a distal end 108 thereof. The distal duckbill seal 112 includes a pair of opposing duckbill members configured to slidingly accept therebetween the distal end portion 16 of the catheter body 12 to form a liquid-tight seal about the catheter body proximal to the distal opening 34. When the distal seal 100 is installed in the flushing chamber 102, however, its sealing passage 124 has a distal opening that is wider than its proximal opening. Moreover, the distal opening of the sealing passage 124 is disposed in the external end of the distal duckbill seal 112 and the proximal opening of the sealing passage 124 is disposed in the tapered end. It should be understood that, though substantially the same components are used for the proximal seal 110 and the distal seal 112, different seals can also be used without departing from the scope of the invention.

Figure 7:
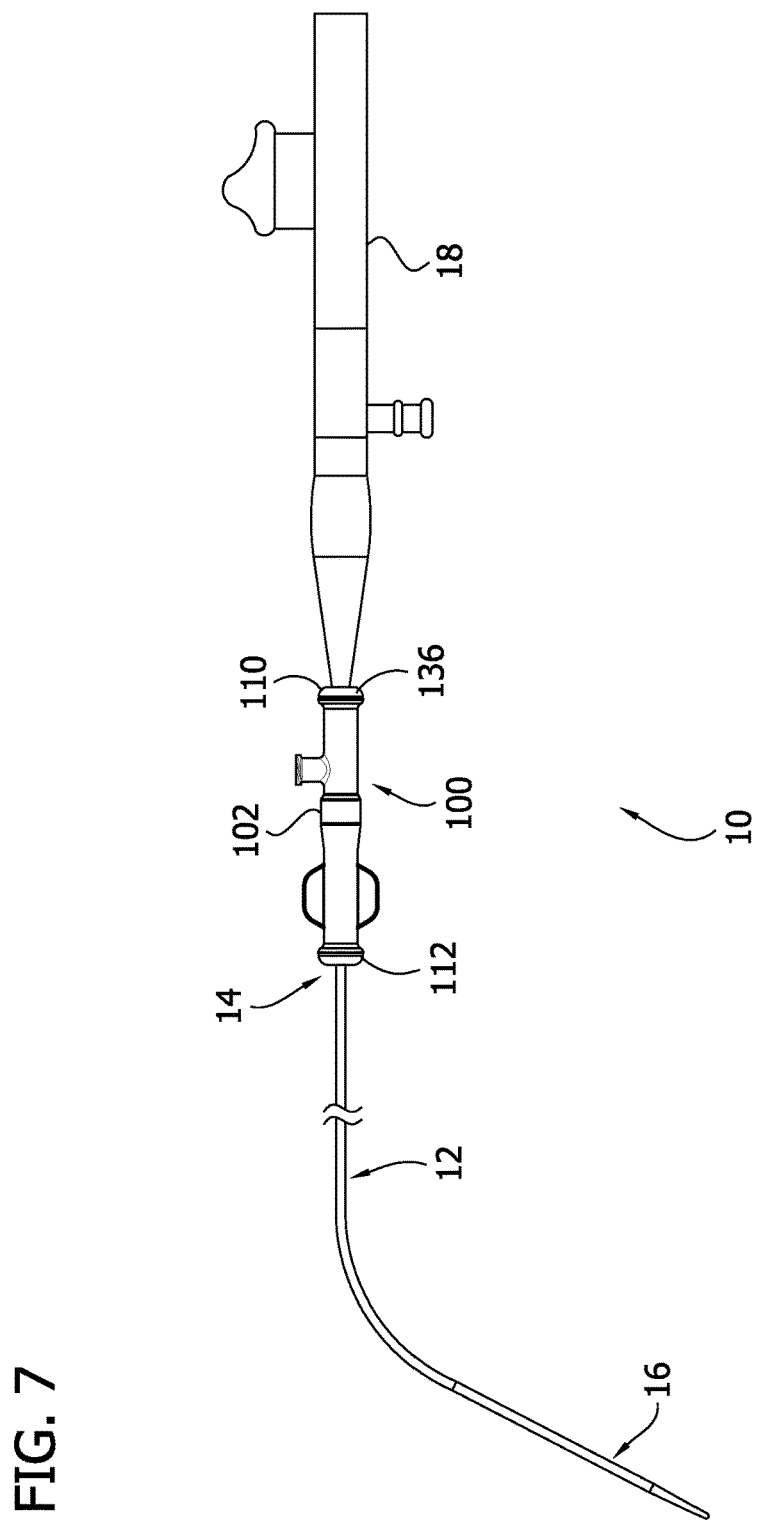
FIG. 7 is a schematic of the cleaning device in a preloaded position on the catheter.

Referring to FIG. 7, in one embodiment, the cleaning device 100 is preloaded on the catheter 10. "Preloaded" means the catheter body 12 extends through the flushing lumen 120 of the cleaning device 100 before the distal end portion 16 of the catheter body is inserted into a biological lumen. When the cleaning device 100 is preloaded it can be moved distally from adjacent the proximal end portion 14 of the catheter body 12 toward the distal end portion 16 of the catheter body to position the cleaning device in the operative position. In the preloaded position, the cleaning device 100 is located generally at the proximal end portion 14 of the catheter body 12. The proximal end portion 14 of the catheter body extends through the flushing lumen 120 of the cleaning device and through the sealing passages 122, 124 of the distal and proximal seals 110, 112 when the cleaning device is in the preloaded position. From the preloaded position, the cleaning device 100 is configured to slide distally along the catheter body 12 until it reaches the operative position. In the illustrated embodiment, the cleaning device 100 cannot slide proximally past the preloaded position. The handle adaptor 18 of the catheter 10 is configured to inhibit the cleaning device 100 from sliding further proximally past the preloaded position. Thus, in the illustrated embodiment, the handle adaptor 18 functions as a stop attached to the proximal end portion 14 of the catheter body 12 and configured to inhibit the cleaning device 100 from sliding proximally past the preloaded position. More specifically, the external end 136 of the proximal duckbill seal 110 is configured to engage the handle adaptor 18 to inhibit the cleaning device 100 from sliding proximally past the preloaded position. The cleaning device can also be inhibited from sliding proximally past the preloaded position in other ways without departing from the scope of the invention. As will be discussed in further detail below, when the cleaning device 100 is in the preloaded position, the catheter 10 is configured to permit the distal end portion 16 of the catheter body 12 to be inserted into a biological lumen until it is positioned adjacent tissue to be removed.

Figure 8:
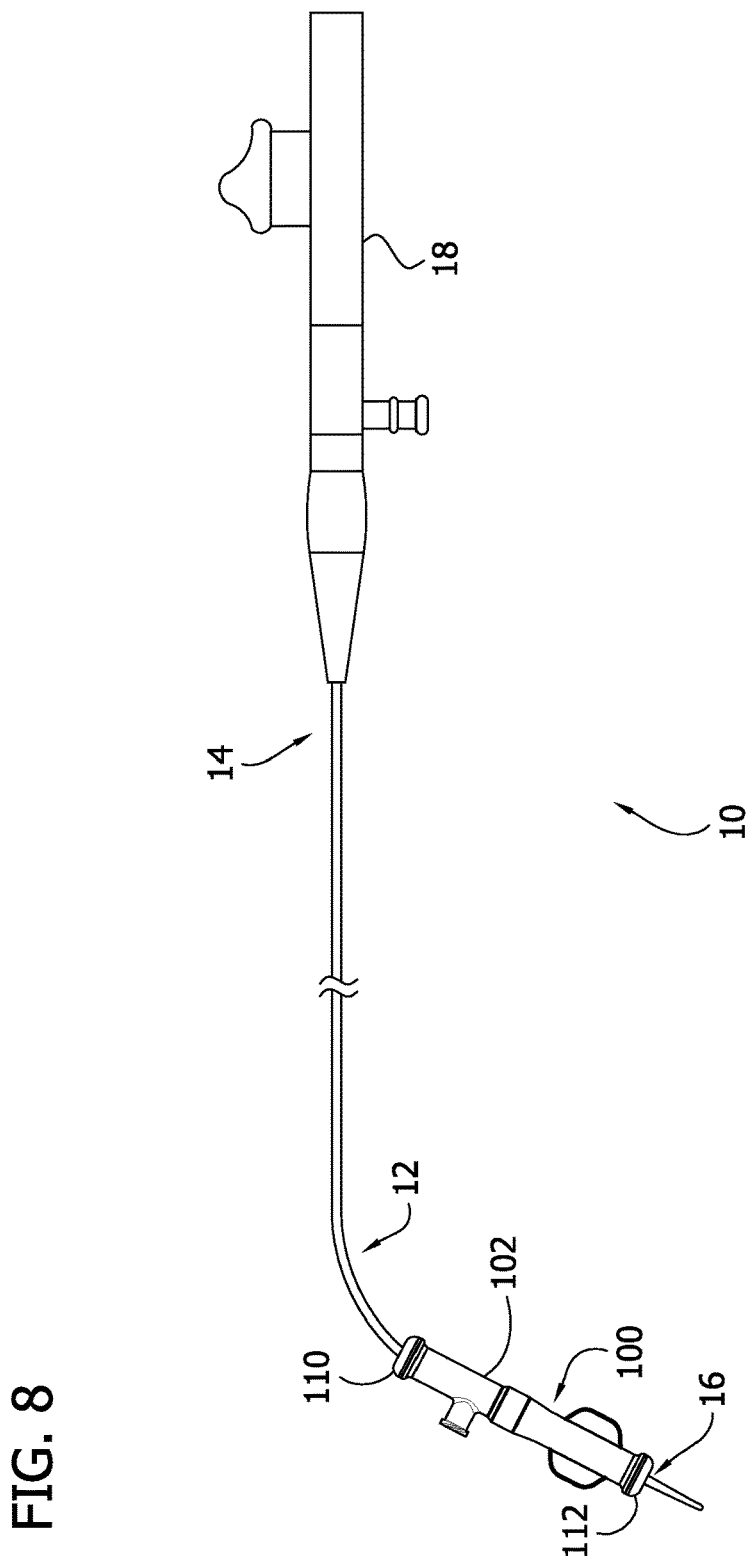
FIG. 8 is a schematic of the cleaning device in an operative position.
Figure 9:
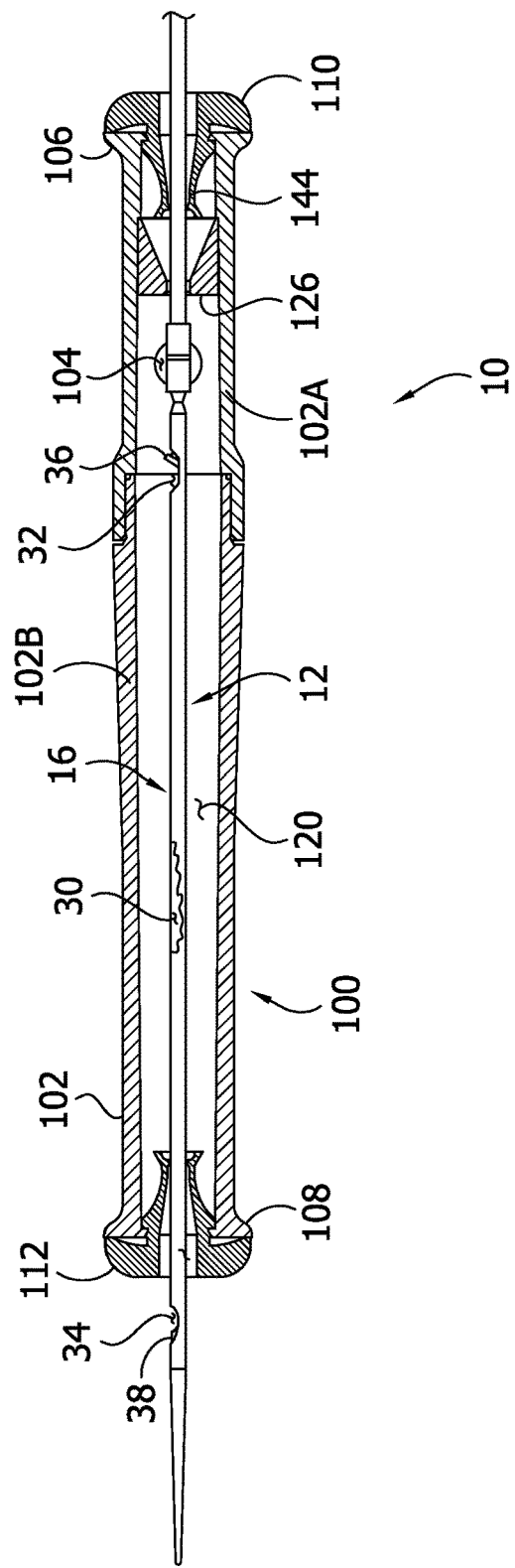
FIG. 9 is a fragmentary partial section view of the cleaning device in the operative position.

The cleaning device 100 is configured to slide from the preloaded position at the proximal end portion 14 of the catheter body 12 to the operative position at the distal end portion 16 of the catheter body, as shown in FIG. 8. Thus, in the illustrated embodiment, the cleaning device 100 is configured to slide in the proximal-to-distal direction toward the operative position. Referring to FIG. 9, in the operative position, the proximal duckbill seal 110 forms a liquid-tight seal (e.g., at the sealing band 144) about the catheter body 12 proximal to the proximal opening 32. Likewise, in the operative position, the distal seal 112 forms a liquid-tight seal about the catheter body 12 distal to the proximal opening 32 and proximal to the distal opening 34. Thus, the proximal opening 32 is disposed between the proximal and distal duckbill seals 110, 112 within the flushing lumen 120, and the distal opening 34 is located distal to the distal duckbill seal outside of the flushing lumen. In the illustrated embodiment, the distal seal 112 forms a liquid-tight seal about the catheter body 12 at a location closer to the distal opening 34 than the proximal opening 32. However, other arrangements can also be used without departing from the scope of the invention.

The cleaning device 100 is configured to fluidly connect a fluid source to the distal end portion 16 of the catheter body 12 and direct fluid from the fluid source into the tissue collection chamber 30 through the proximal and distal openings 32, 34 to facilitate cleaning of the tissue collection chamber. In the operative position of the illustrated embodiment, the proximal and distal openings 32, 34 form a fluid inlet and fluid outlet, respectively, of the tissue collection chamber 30. The cleaning device 100 is configured to receive fluid that is directed into the inlet port 104 and that thereby enters the flushing lumen 120. The proximal and distal duckbill seals 110, 112 are configured to prevent the fluid from escaping the flushing lumen out the open ends 106, 108 of the cleaning device 100. In the operative position, the proximal opening 32 is disposed between the distal and proximal seals 110, 112 and is configured to receive the fluid in the flushing lumen 120 such that the fluid flows through the tissue collection chamber 30 and out the distal opening 34. The pressure of the fluid in the tissue collection chamber 30 directs tissue contained therein out the distal opening along with the fluid.

Though in the illustrated embodiment the proximal opening 32 of the distal end portion 16 of the catheter body 12 is disposed within the flushing lumen 120 and the distal opening 34 is disposed outside the flushing lumen in the operative position, in other embodiments a cleaning device can be arranged differently with respect to a catheter body in the operative position. For example, in one embodiment, a distal opening of a distal end portion of a catheter body is disposed within a flushing lumen of a cleaning device and a proximal opening of the distal end portion of a catheter body is disposed outside the flushing lumen of the cleaning device in the operative position. In this embodiment, the cleaning device is configured for fluid to flow in an inlet of the cleaning device, into the flushing lumen, in the distal opening of the distal end portion of the catheter body, through a tissue collection chamber, and out the proximal opening of the distal end portion of the catheter body.

As illustrated in FIG. 9, in the operative position, the external stop 40 of the catheter 10 is engages the internal stop 126 of the cleaning device 100 to inhibit the cleaning device from sliding distally past the operative position. In certain embodiments, the cleaning device 100 is entirely inhibited from sliding distally past the operative position, such that further sliding would cause breakage of one or both of the internal stop 126 and the external stop 40. In other embodiments, the cleaning device 100 is partially inhibited from sliding distally past the operative position, such that, depending on the angular alignment of the cleaning device 100 and catheter body 12, the internal stop 126 will engage or fail to engage the external stop 40. In the illustrated embodiment, engagement between the external stop 40 of the catheter body 12 and the internal stop 126 of the cleaning device 100 positions the cleaning device in the operative position with respect to the catheter body. Thus, a user can merely slide the cleaning device 100 from the preloaded position distally until the internal stop 126 of the cleaning device engages the external stop 40 of the catheter body 12 to position the cleaning device in the operative position. This greatly simplifies the process of flushing the tissue collection chamber 30 of its contents. The user is no longer required to visually determine proper positioning between the cleaning device 100 and the catheter body 12 because the engagement between the internal stop 126 and the external stop 40 provides an easy-to-identify and precise indication of proper positioning. Positioning errors and flushing procedure time are, thus, greatly reduced.

Though in the illustrated embodiment the cleaning device 100 is preloaded on the catheter body 12, in other embodiments the cleaning device can be unloaded. For example, the cleaning device 100 can have an unloaded position in which the cleaning device is disconnected from the catheter body 12. In the unloaded position, no portion of the catheter body 12 is disposed within or extends through the flushing lumen 120 of the cleaning device 100. The cleaning device 100 can be configured to slide from the unloaded position disconnected from the catheter body 12 to an operative position at the distal end portion 16 of the catheter body. More specifically, the tip of the distal end portion 16 can be inserted into the proximal opening 140 of the sealing passage 122 of the proximal duckbill seal 110 and the distal end portion of the catheter body can be inserted through the flushing lumen 120 and sealing passage 124 of the distal seal 112 until the cleaning device reaches the operative position. In this embodiment the cleaning device 100 slides along the catheter body 12 toward the operative position in the distal-to-proximal direction. It is contemplated that, in this embodiment, an internal stop of the cleaning device could be arranged to engage an external stop of the catheter body when the cleaning device is positioned in the operative position.

In one embodiment of a method of using the catheter 10, a distal end portion 16 of the catheter body 12 is inserted into an incision and further into a biological lumen of a patient (e.g., an artery). The catheter body 12 is moved along the biological lumen until the distal end portion 16 is positioned adjacent tissue to be removed. Using controls disposed on the handle adaptor 18 and/or handle (not shown), the cutting element 36 of the catheter 10 is positioned to operatively engage tissue to be removed. A driver (not shown) of the catheter 10 is subsequently actuated using the controls, which causes the cutting element 36 to rotate about its longitudinal axis to slice away the tissue. Simultaneously, the catheter body 12 is inserted distally further into the biological lumen. The excised tissue is directed into the tissue collection chamber 30 until it is filled. One skilled in the art will appreciate that "filled" does not require the entire volume of the tissue collection chamber to be occupied by tissue. Once the tissue collection chamber 30 is filled, the catheter body 12 is drawn out of the biological lumen.

The present embodiment of a method of using the catheter 10 includes performing the steps of a method of cleaning the collected cut tissue from the tissue collection chamber 30. Once the catheter body 12 has been removed from the biological lumen, the cleaning device 100 is positioned in the operative position with respect to the catheter body 12. In one embodiment, the preloaded cleaning device 100 is slid from its preloaded position (FIG. 7) to its operative position (FIG. 8). For example, the preloaded cleaning device 100 is slid distally along the catheter body 12 until the internal stop 126 of the cleaning device engages the external stop 40 of the catheter body 12. In another embodiment, an unloaded cleaning device 100 is slid proximally from the unloaded position to the operative position with respect to the catheter body 12. For example, the tip of the distal end portion 16 of the catheter body 12 is inserted into the sealing passage 122 of the proximal duckbill seal 110, through the flushing lumen 120, and out the sealing passage 124 of the distal duckbill seal 112.

Once the preloaded cleaning device 100 reaches its operative position, its proximal duckbill seal 110 passively forms a liquid-tight seal with the distal end portion 16 of the catheter body 12, without any additional sealing actuation. Likewise, the distal duckbill seal 112 passively forms a liquid-tight seal with the distal end portion 18 of the catheter body 12, without any additional sealing actuation. The proximal duckbill seal 110 compressively conforms to the cross-sectional shape of the catheter body 12 at the sealing band 144. In the operative position, the proximal duckbill seal 110 forms a liquid-tight seal with the catheter body 12 proximal to the proximal opening 32 of the distal end portion 16 of the catheter body 12. The distal duckbill seal 112 forms a liquid-tight seal distal to the proximal opening 32 of the distal end portion 16 of the catheter body 12 and proximal to the distal opening 34 of the distal end portion of the catheter body. With the cleaning device 100 in the operative position, flushing fluid is imparted through the fluid inlet port 104 and into the flushing lumen 120. The flushing fluid at least partially fills the flushing lumen 120 and is directed into the tissue collection chamber 30 through the proximal opening 32. The flushing fluid flows through the tissue collection chamber 30 and out the distal opening 34 of the distal end portion 16 of the catheter body 12. As it flows through and out of the tissue collection chamber 30, the flushing fluid expels tissue contained in the tissue collection chamber 30 out the distal opening 34.

Figure 10:
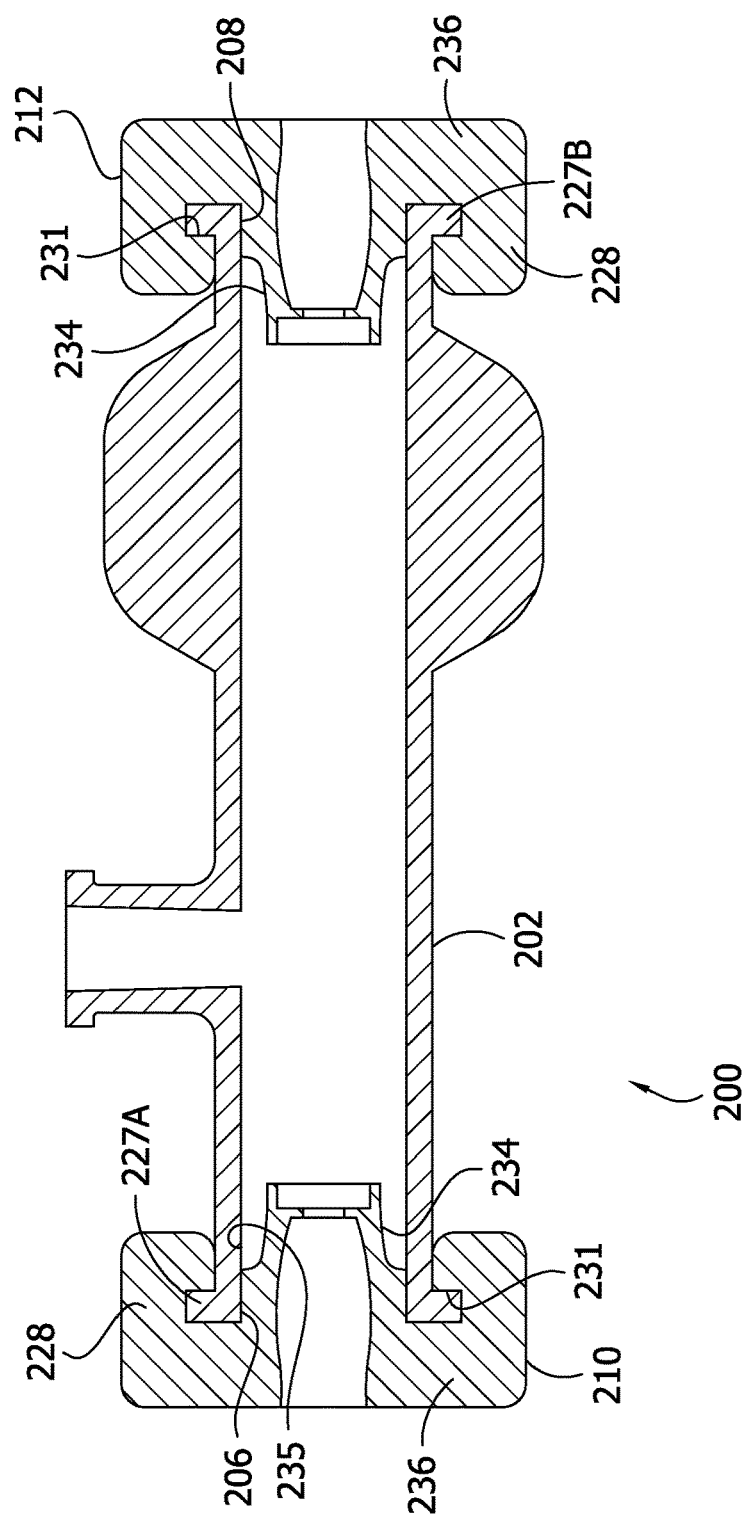
FIG. 10 is section view of another embodiment of a cleaning device.

Referring to FIG. 10, another embodiment of a cleaning device is generally indicated at reference number 200. The cleaning device 200 is substantially similar to the flush tool 100, except for the differences that are, in part, apparent and, in part, pointed out hereinafter. Features of the cleaning device 200 that correspond with features of the cleaning device 100 are given the same reference number, plus 100. Like the cleaning device 100, the cleaning device 200 is configured to receive the catheter body 12 and to direct flushing fluid through the tissue collection chamber 30 to discharge debris from the tissue collection chamber. Unlike the cleaning device 100, the cleaning device 200 includes a one-piece flushing chamber 202. The flushing chamber 202 has an open proximal end 206 and an open distal end 208. In a preferred embodiment, the cleaning device is formed in an injection molding process using a single core pin, for example. Whereas the flushing chamber 102 includes two internal annular seal retention lips 127A, 127B that extend radially inward adjacent the ends 106, 108 thereof, the flushing chamber 202 includes a proximal external annular seal retention flange or lip 227A and a distal external annular seal retention flange or lip 227B that extend radially outwardly adjacent the proximal end 206 and distal end 208, respectively.

The cleaning device 200 includes proximal and distal seals 210, 212 that function substantially similar to the seals 110, 112. Each of the seals 210, 212 has an internal end 234 that is sealingly received in the respective open end 206, 208 of the flushing chamber 202 and an external end 236 that protrudes from the flushing chamber. The internal end 234 of each of the seals 210, 212 engages the interior surface of the flushing chamber to form a seal interface therewith. Preferably, the internal ends 234 of the seals 210, 212 are held in compression to form a tight seal with the respective ends 206, 208 of the flushing chamber 202. An annular retention formation 228 extends axially inwardly from the external end 236 of each of the seals 210, 212 to grip the respective seal retention lip 227A, 227B and thereby secure the seal to the flushing chamber 127. Each of the retention formations 228 includes an elbow defining an axially outward facing engagement surface 231. The axially outward facing engagement surface 231 engages an annular, axially inward facing surface of the respective seal retention lip 227A, 227B. The engagement between the engagement surface 231 and the retention lip 227A secures the proximal seal 210 to the flushing chamber 202 and inhibits the proximal seal from being removed from the proximal end 206 of the flushing chamber. Likewise, the engagement between the engagement surface 231 and the retention lip 127B secures the distal seal 212 to the distal end 208 of the flushing chamber 202.

Figure 11:
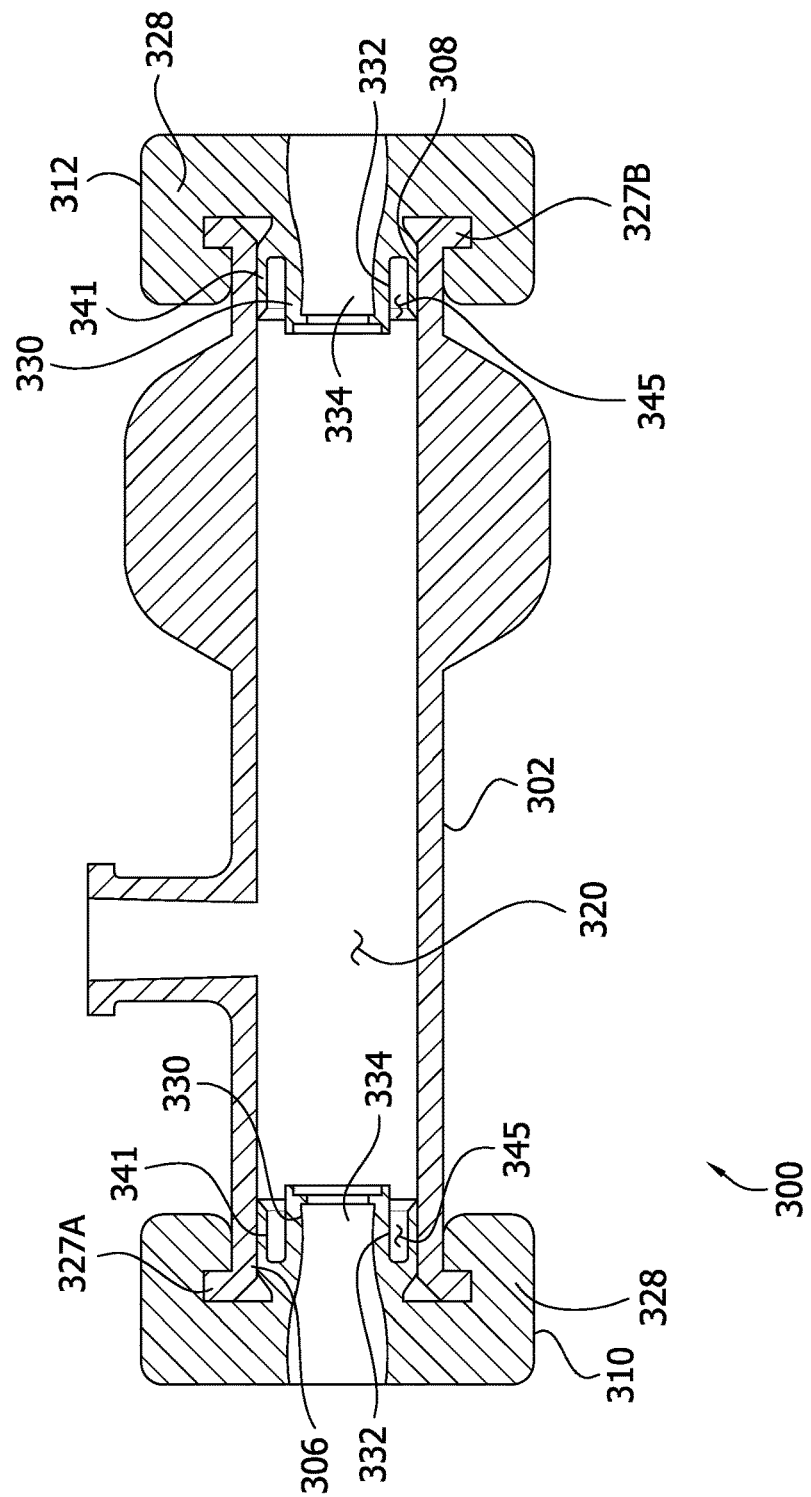
FIG. 11 is a section view of another embodiment of a cleaning device.

Referring to FIG. 11, another embodiment of a cleaning device is indicated generally at reference number 300, The cleaning device 300 is substantially similar to the cleaning device 200, except for the differences that are, in part, apparent and, in part, pointed out hereinafter. Features of the cleaning device 300 that correspond with features of the cleaning device 200 are given the same reference number, plus 100. Like the cleaning device 200, the cleaning device 300 includes a one-piece flushing chamber 302 and proximal and distal seals 310, 312 and is configured to direct flushing fluid through the tissue collection chamber 30 of the catheter body 12. Each of the seals 310, 312 includes an annular retention formation 328 that grips a respective one of the retention lips 327A, 327B to secure the seal to the respective end 306, 308 of the flushing chamber 302.

The internal end portions 334 of the seals 310, 312 are configured to sealingly engage the interior of the flushing chamber 302. Moreover, as fluid pressure in the flushing lumen 320 increases, the tightness of the seal interfaces between the seals 310, 312 and the flushing chamber 302 also increases. Each of the seals 310, 312 includes an annular sealing skirt 341 that sealingly engages the interior surface of the flushing chamber 302. The sealing skirt 341 surrounds and is spaced radially from the opposing duckbill members 330, 332. A generally annular void 345 is defined between the sealing skirt 341 and the duck bill members 330, 332. When each of the seals 310, 312 is installed in the flushing chamber 302, the void 345 is in fluid communication with the flushing lumen 320. When fluid fills the flushing lumen 320, the fluid likewise fills the annular voids 345. A positive pressure urges the generally axially extending portions of the skirts 341 radially outward against the flushing chamber, thereby enhancing the sealing engagement between the sealing skirts and the flushing chamber. A positive pressure in the annular voids 345 also urges the duck bill members 330, 332 inward to enhance sealing engagement with the catheter body 12 received therebetween. An inner, free end of each of the sealing skirts 341 is chamfered to prevent pressurized fluid in the flushing chamber 320 from imparting a generally axially oriented force on the end of the sealing skirts that may tend to cause the sealing skirt to buckle and lose its seal with the flushing chamber 302.

Figure 12:
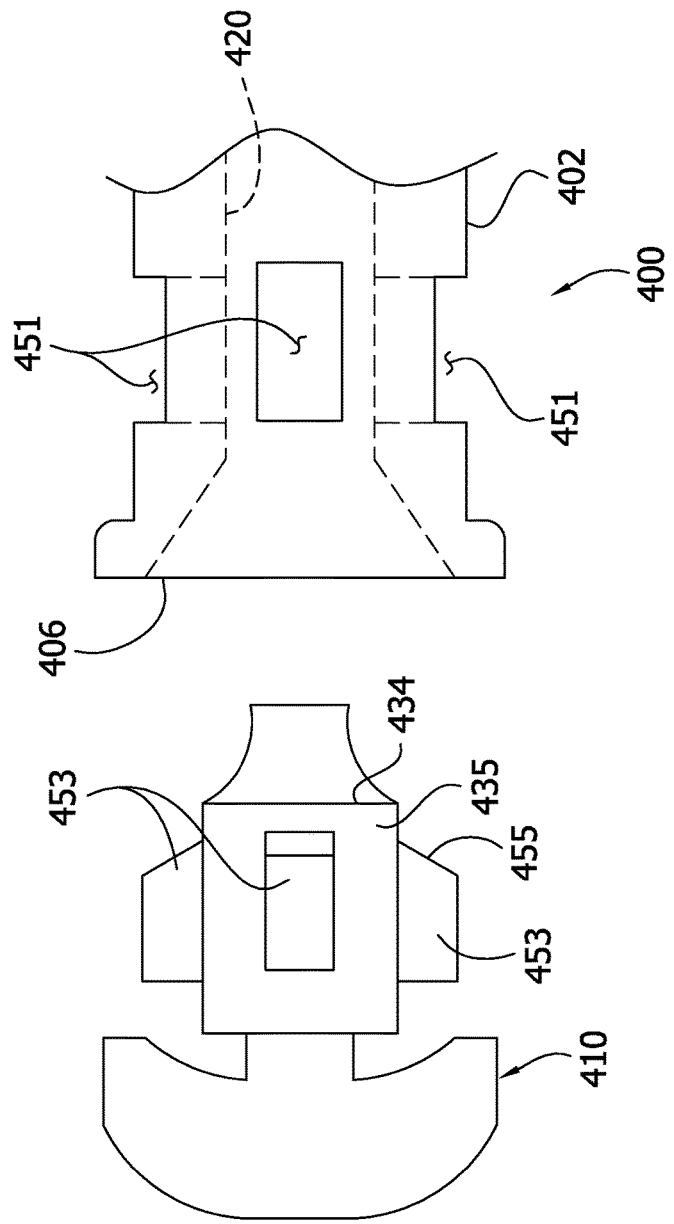
FIG. 12 is a fragmentary exploded side elevation view of another embodiment of a cleaning device.

Referring to FIG. 12, another embodiment of a cleaning device is generally indicated at reference number 400. Although not illustrated in its entirety, like the cleaning device 200, the cleaning device 400 preferably includes a one-piece flushing chamber 402 and proximal and distal seals (only the proximal seal 410 is shown in FIG. 12) configured to form a seal around portions of the catheter body 12 as the catheter body extends through the flushing lumen 420. Unlike the flushing chamber 202, the flushing chamber 402 does not include a seal retention lip. Instead, four slots 451, which are angularly spaced apart around the circumference of the flushing chamber 402, extend radially through the wall of the flushing chamber adjacent the proximal end 406 thereof. Each of the four slots 451 adjacent the proximal end 406 of the flushing chamber 402 is configured to receive a respective one of four lugs 453 that extends radially outwardly from a stem portion 435 of the internal end portion 434 of the proximal seal 410. The stem portion 435 is sized to sealingly engage the flushing chamber 402 when the seal 410 is received in the open proximal end. The inner axial ends 455 of the lugs 453 slope radially inward to enable the seal 410 to be inserted into the open proximal end 406 of the flushing chamber 402. The lugs 453 of the seal 410 are received in the slots 451 when the seal is secured to the flushing chamber. The lugs 453 engage the flushing chamber 402 within the slots 451 to inhibit the seals from being dislodged outwardly from the open end 406 of the flushing chamber when the flushing lumen 420 is filled with a pressurized fluid. Although the illustrated embodiment uses four rectangular shaped slots 451 and four rectangular shaped lugs 453, other embodiments can use other numbers and configurations of slots and lugs without departing from the scope of the invention. The distal end (not shown) of the flushing chamber 402 may also include slots for receiving a distal seal (not shown) comprising correspondingly positioned lugs, or the distal end could include another structure for securing the distal seal without departing from the scope of the invention.

Figure 13:
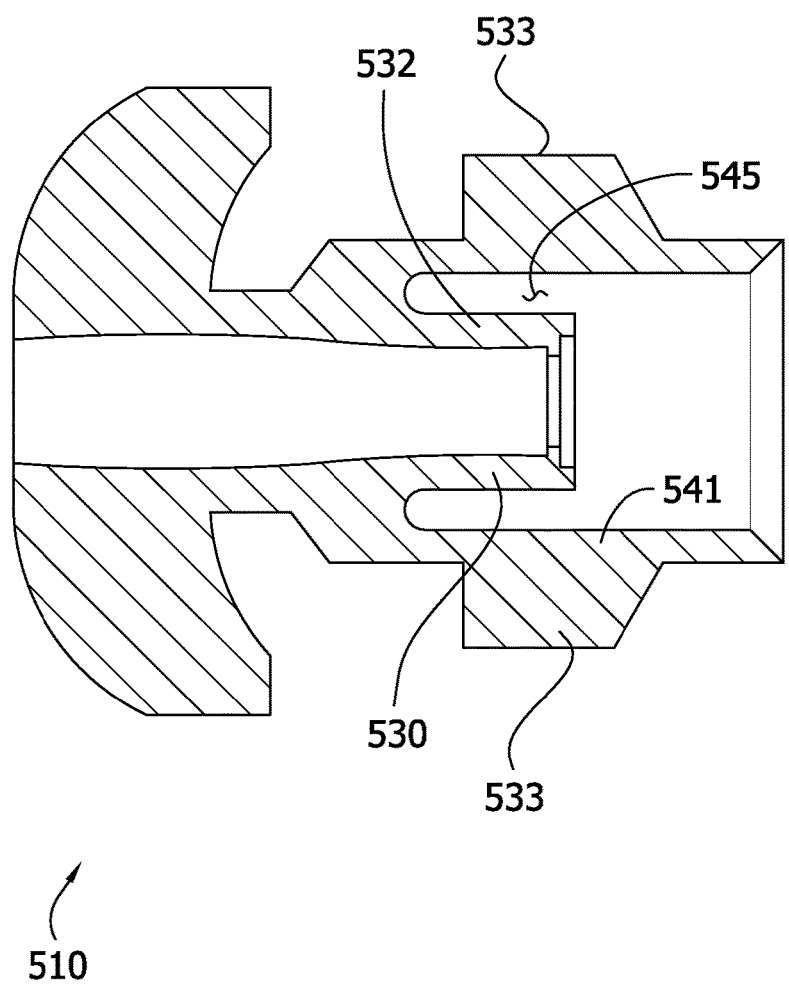
FIG. 13 is a section view of a seal for use with a cleaning device.

Referring to FIG. 13, another embodiment of a seal is generally indicated at reference number 510. Like the seal 410, the seal 510 includes radially outwardly extending lugs 553 configured to be received in correspondingly positioned slots in a flushing chamber (e.g., the flushing chamber 402) to secure the seal to the flushing chamber. But unlike the seal 410, the lugs 553 of the seal 510 extend radially outwardly from an annular sealing skirt 541 that surrounds and is spaced radially from the duck bill members 530, 532. When the seal 510 is secured to the flushing chamber, the sealing skirt 541 sealingly engages the interior surface of the flushing chamber. The sealing skirt 541 is configured so that the tightness of the sealing engagement with the flushing chamber increases as fluid pressure in the flushing lumen increases. A generally annular void 545 extends between the skirt 541 and the duck bill members 530, 532. When the seal 510 is installed in a flushing chamber, the void 545 is fluidly coupled to the flushing lumen. When fluid fills the flushing lumen, the fluid likewise fills the annular void 545. A positive pressure in the void 545 urges the generally axially extending portion of the skirt 541 radially outwardly, thereby enhancing the sealing engagement between the skirt and the flushing chamber. Moreover, since the lugs 553 extend from the skirt 541, positive pressure in the flushing lumen also urges the lugs radially outwardly, thereby enhancing the engagement between the lugs 553 and the flushing chamber. Although in the illustrated embodiment, the sealing skirt 541 is an annular skirt, it is also contemplated that each of the lugs 553 could be mounted on a separate flap that contacts the inner surface of the flushing chamber and is exposed to the flushing lumen so that a positive pressure in the flushing lumen urges the flap outwardly to improve engagement between the supported lug and the respective slot.

Figure 14:
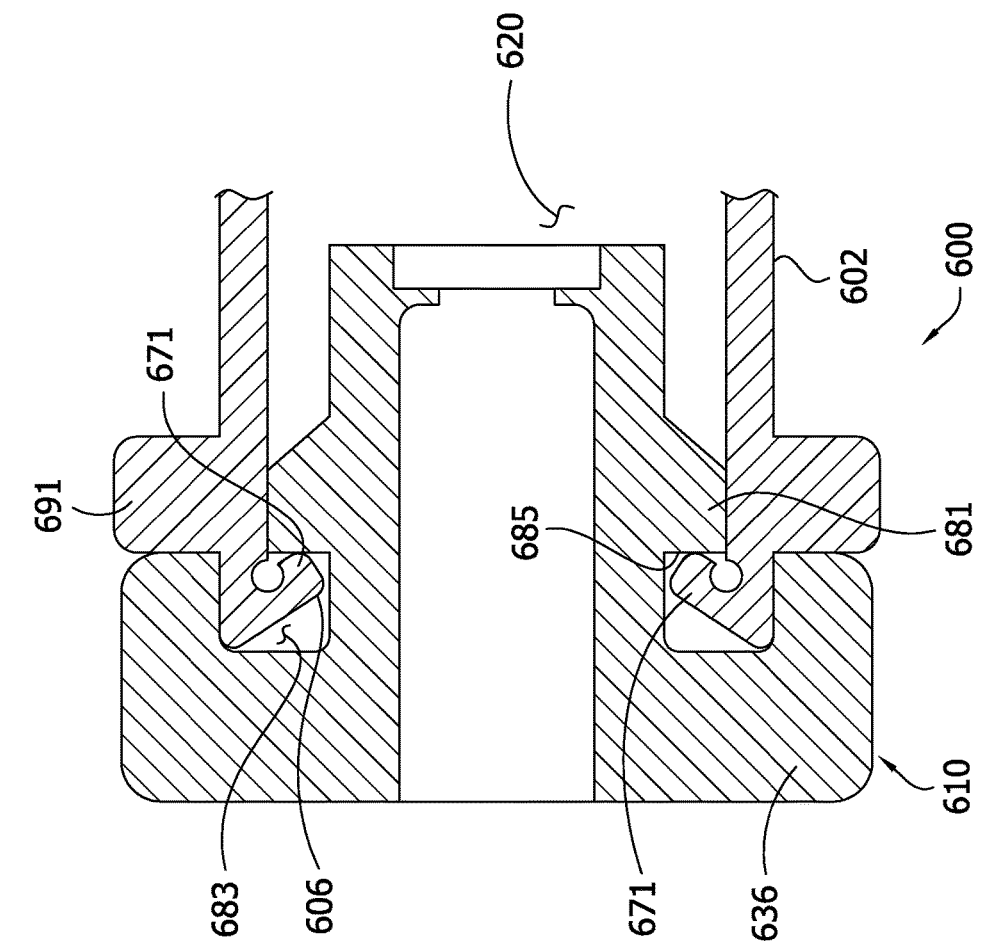
FIG. 14 is a fragmentary section of another embodiment of a cleaning device.
Figure 15:
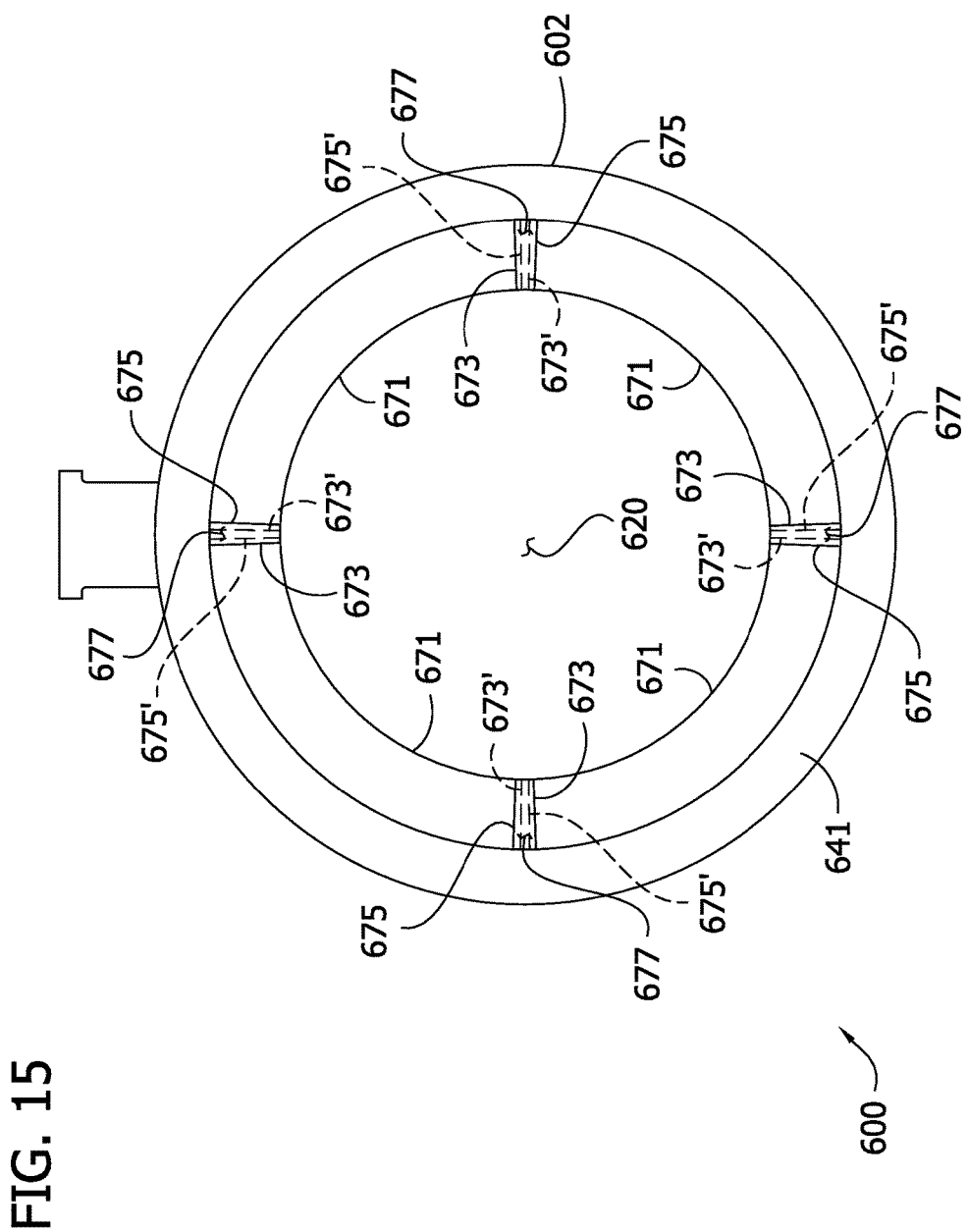
FIG. 15 is an end elevation of a flushing chamber of the cleaning device of FIG. 14 illustrating tabs of the flushing chamber in a fully bent position and using broken lines to illustrate the edges of the tabs when bent outward from the fully bent position to an intermediate position.

Referring to FIGS. 14-15, another embodiment of a cleaning device is generally indicated at reference number 600. The cleaning device 600 is substantially similar to the cleaning device 100, except for differences that are, in part, apparent and, in part, pointed out hereinafter. Features of the cleaning device 600 that correspond with features of the cleaning device 100 are given the same reference number, plus 500. Like the cleaning device 100, the cleaning device 600 includes a flushing chamber 602 and proximal and distal seals (only the proximal seal 610 is illustrated in FIG. 14) that are respectively secured to the open proximal and distal ends (only the proximal end 606 is illustrated in FIGS. 14 and 15) of the flushing chamber. When the catheter body 12 extends through flushing lumen 620 of the cleaning device 600, the seal 610 seals around the catheter body to seal the open proximal end 606 of the flushing chamber 602. The distal end of the flushing chamber 602 could have the same construction as or a different construction than the proximal end 606.

Although the cleaning device 600 preferably functions similar to the cleaning device 100, unlike the flushing chamber 102, the proximal end 606 of the flushing chamber 602 includes bendable retention tabs 671 for securing the proximal seal 610 to the flushing chamber. In the illustrated embodiment, the proximal end 606 of the flushing chamber 602 defines four retention tabs 671 that are spaced around the circumference of the flushing chamber wall. In other embodiments, the cleaning device has other numbers of bendable retention tabs without departing from the scope of the invention. The retention tabs 671 are bendable from a first position (not shown) in which the retention tabs extend substantially parallel to the longitudinal axis of the flushing chamber 602 to a second position (FIGS. 14 and 15) in which the retention tabs extend radially inward toward the center of the flushing chamber. When the retention tabs 671 are bent to the second position, they function like a retention lip for securing the seal 610 to the flushing chamber 602. In the illustrated embodiment, the retention tabs 671 are bent inward at an angle of greater than 90° relative to the longitudinal axis of the flushing chamber 602 in the second, bent position. The retention tabs 671 may include a zone of weakness (e.g., a recessed portion) along a bend line to facilitate bending of the retention tabs at the desired location.

As shown in FIG. 15, each of the retention tabs 671 has a first edge 673 and a second edge 675. When the retention tabs 671 are fully bent to the second position, the first edge 673 of one tab is separated from the adjacent second edge 675 of another tab by a relatively small gap 677. But as illustrated by the dotted lines in FIG. 15, at an intermediate position between the first position and second position (e.g., a position at which the tabs 671 are oriented at about 90° relative to the longitudinal axis of the flushing chamber 602), an edge margin of each of the tabs adjacent the first edge 673' interferes with an edge margin adjacent the second edge 675' of the adjacent tab. As discussed below, the interference between the tabs 671 at the intermediate position inhibits the tabs from bending away from the second position when the seal 610 is secured to the proximal end 606 of the flushing chamber 602.

The seal 610 is configured to engage retention tabs 671 bent to the second position to secure the seal to the proximal end 606 of the flushing chamber 602. Referring to FIG. 14, the seal 610 includes an annular projection 681 that extends radially outward from the internal end portion 634 of the seal and is configured to sealingly engage the interior surface of the flushing chamber 602. The annular projection 681 and external end portion 636 of the seal define an annular groove 683. When the seal 610 is secured to the flushing chamber 602, each of the tabs 671 is received in the groove 683 in the second position. When the seal 610 is in the proper position, the external end portion 636 of the seal 610 engages an annular stop 691 extending radially outwardly near the end 606 of the flushing chamber 602. The tabs 671 engage an axially facing engagement surface 685 of the projections 681 to inhibit the seal from sliding outwardly from the end 606 of the flushing chamber 602. Because the tabs 671 are bent to an angle of greater than 90° when in the second position, the outward axial forces exerted on the seal 610 due to positive pressure in the flushing lumen act in compression against the tabs 671, rather than purely to impart a bending moment on the tabs. It is believed that the tabs 671 are less prone to bending back toward the first position as a result of compressive forces imparted thereupon than in response to a bending moment imparted thereupon. If the seal 606 is displaced axially outwardly, all of the tabs 671 are bent away from the second position at the same time, and adjacent edge margins of the each of the tabs interfere with one another as the tabs are bent back toward 90° relative to the longitudinal axis of the flushing chamber 602. It is believed that the interference between the edge margins of the tabs inhibits the tabs from bending from the second position to and/or past 90°. Thus, the bendable tabs 671 are configured to resist bending from the second position toward the first position when the seal 610 is secured to the flushing chamber 602.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A cleaning device for cleaning a catheter comprising a catheter body having a distal end portion defining a catheter lumen and proximal and distal openings in fluid communication with the catheter lumen, the cleaning device comprising:
  a flushing chamber having opposite proximal and distal ends, a flushing lumen extending between the proximal and distal ends, and an inlet port in fluid communication with the flushing lumen, wherein the flushing lumen is configured to accept the distal end portion of the catheter body therein through the proximal end thereof;
  a proximal duckbill seal sealingly received in the flushing lumen at a location proximal of the inlet port, the proximal duckbill seal including a pair of opposing duckbill members configured to slidingly accept therebetween the distal end portion of the catheter body to form a proximal fluid seal about the catheter body at a location proximal of the inlet port; and
  a distal duckbill seal sealingly received in the flushing lumen at a location distal of the inlet port such that the inlet port is located between the proximal duckbill seal and the distal duckbill seal, the distal duckbill seal being configured to form a distal fluid seal about the catheter body, the distal duckbill seal including a pair of opposing duckbill members configured to slidingly accept therebetween the distal end portion of the catheter body to form the distal fluid seal about the catheter body;
  wherein each of the proximal fluid seal and the distal fluid seal is configured to prevent fluid in the flushing lumen from passing therethrough,
  wherein the pair of opposing duckbill members defines a tapered distal end of the proximal duckbill seal,
  wherein the pair of opposing duckbill members of the distal duckbill seal defines a tapered proximal end of the distal duckbill seal.

2. The cleaning device of claim 1 wherein the cleaning device is configured to slide from a preloaded position at a proximal end portion of the catheter body to an operative position at the distal end portion of the catheter body.

3. The cleaning device of claim 2 further comprising an internal stop configured to engage an external stop of the catheter body to inhibit the cleaning device from sliding distally along the catheter body away from the proximal end portion thereof past the operative position.

4. The cleaning device of claim 2 wherein the proximal duckbill seal is configured to engage a stop attached to the proximal end portion of the catheter body to inhibit the cleaning device from sliding proximally along the catheter body away from the distal end portion thereof past the preloaded position.

5. The cleaning device of claim 1 wherein the cleaning device is configured to slide from an unloaded position disconnected from the catheter body to an operative position at the distal end portion of the catheter body.

6. The cleaning device of claim 5 wherein the cleaning device is configured to slide in a distal-to-proximal direction from the unloaded position to the operative position.

7. The cleaning device of claim 1 wherein the proximal duckbill seal comprises a one-piece body of material.

8. The cleaning device of claim 7 wherein said material is an elastomeric material.

9. The cleaning device of claim 1 wherein the proximal duckbill seal comprises a sealing passage between the pair of opposing duckbill members, the sealing passage having open proximal and distal ends and being generally tapered from its proximal end to its distal end.

10. The cleaning device of claim 9 wherein the proximal duckbill seal is configured to form said fluid seal about the catheter body at a sealing band of the sealing passage that defines an opening having an equilibrium cross-sectional shape that is smaller than a cross-sectional shape of the catheter body received in the proximal duckbill seal.

11. The cleaning device of claim 10 wherein the sealing band is configured to have a sealing cross-sectional shape that compressively conforms to said cross-sectional shape of the catheter body received in the proximal duckbill seal.

12. The cleaning device of claim 1 wherein the proximal duckbill seal is axially fixed with respect to the flushing chamber.

13. The cleaning device of claim 1 in combination with the catheter, wherein the catheter further has a proximal end portion opposite the distal end portion, wherein the cleaning device is received on the proximal end portion of the catheter body and configured to slide from a preloaded position at the proximal end portion of the catheter body to an operative position at the distal end portion of the catheter body.

14. The cleaning device in combination with the catheter as set forth in claim 13, wherein the catheter body comprises an external stop configured to engage an internal stop of the cleaning device to inhibit the cleaning device from sliding distally past the operative position and to position the cleaning device in the operative position.

15. The cleaning device in combination with the catheter as set forth in claim 13, wherein the catheter further comprises a cutter at the distal end portion of the catheter body, wherein the proximal opening comprises a cutter window through which the cutter is configured to extend.

* * * * *